US009511947B2

(12) United States Patent
Pollack et al.

(10) Patent No.: US 9,511,947 B2
(45) Date of Patent: Dec. 6, 2016

(54) LINEAR RANDOM ACCESS QUEUE

(71) Applicants: Benjamin Samuel Pollack, Budd Lake, NJ (US); Colin Mellars, Dover, NJ (US); Baris Yagci, Whippany, NJ (US)

(72) Inventors: Benjamin Samuel Pollack, Budd Lake, NJ (US); Colin Mellars, Dover, NJ (US); Baris Yagci, Whippany, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 102 days.

(21) Appl. No.: 14/402,942

(22) PCT Filed: May 20, 2013

(86) PCT No.: PCT/US2013/041910
§ 371 (c)(1),
(2) Date: Nov. 21, 2014

(87) PCT Pub. No.: WO2013/177087
PCT Pub. Date: Nov. 28, 2013

(65) Prior Publication Data

US 2015/0166265 A1 Jun. 18, 2015

Related U.S. Application Data

(60) Provisional application No. 61/650,015, filed on May 22, 2012.

(51) Int. Cl.

| | |
|---|---|
| ***G01N 35/00*** | (2006.01) |
| ***B65G 43/00*** | (2006.01) |
| ***G01N 35/04*** | (2006.01) |
| ***G05B 15/02*** | (2006.01) |

(52) U.S. Cl.
CPC ........... *B65G 43/00* (2013.01); *G01N 35/0092* (2013.01); *G01N 35/0095* (2013.01); *G01N 35/04* (2013.01); *G05B 15/02* (2013.01); *G01N 2035/0094* (2013.01); *G01N 2035/0462* (2013.01); *G01N 2035/0472* (2013.01)

(58) Field of Classification Search
None
See application file for complete search history.

(56) References Cited

U.S. PATENT DOCUMENTS

| | | | | |
|---|---|---|---|---|
| 5,350,564 | A * | 9/1994 | Mazza | ................ B01L 3/50855 422/562 |
| 5,735,387 | A | 4/1998 | Polaniec et al. | |
| 6,334,358 | B2 | 1/2002 | Muraoka et al. | |
| 7,186,378 | B2 | 3/2007 | Dunfee | |
| 2002/0146347 | A1 | 10/2002 | McNeil | |
| 2008/0040151 | A1 | 2/2008 | Moore | |

(Continued)

FOREIGN PATENT DOCUMENTS

| | | |
|---|---|---|
| EP | 0 753 747 A2 | 1/1997 |
| EP | 1 109 006 A2 | 6/2001 |

(Continued)

OTHER PUBLICATIONS

PCT International Search Report and Written Opinion dated Nov. 29, 2013 (8 Pages).

(Continued)

*Primary Examiner* — Robert R Raevis

(57) ABSTRACT

Methods and systems for managing queues of sample carriers in a bidirectional track allow queues to behave as linear FIFO queues while providing random access to samples by resorting samples in the queue. One or more storage positions to allow sample carriers to be selectively removed and reinserted into the queue, allowing the order of sample carriers to be resorted.

13 Claims, 24 Drawing Sheets

510 534 540 530 A B C D 532 544
510 534 B 541 530 A C D 532 545
510 534 542 530 A C B D 532 546

(56) References Cited

U.S. PATENT DOCUMENTS

2008/0271546 A1 11/2008 Miller et al.
2011/0104742 A1 5/2011 Fox et al.

FOREIGN PATENT DOCUMENTS

EP 1 881 329 A2 1/2008
EP 2 148 204 A1 1/2010
JP 2009 008552 A 1/2009

OTHER PUBLICATIONS

Extended EP Search Report dated Jan. 27, 2016 of corresponding European Application No. 13793701.7, 6 Pages.

* cited by examiner 200
204
217
211B
215
206B
208B
214
210B
216
205B
206
208
210
205
206A
208A
210A
205A
220
202
222

601

| Storage | -, 2 | | | | | | | |
|---|---|---|---|---|---|---|---|---|
| Sample | A | B | C | D | E | - | - | - |
| Position | 0 | 1 | 2 | 3 | 4 | 5 | 6 | 7 |

602

| Storage | C, 2 | | | | | | | |
|---|---|---|---|---|---|---|---|---|
| Sample | A | B | - | D | E | - | - | - |
| Position | 0 | 1 | 2 | 3 | 4 | 5 | 6 | 7 |

603

| Storage | C, 0 | | | | | | | |
|---|---|---|---|---|---|---|---|---|
| Sample | - | A | B | D | E | - | - | - |
| Position | 0 | 1 | 2 | 3 | 4 | 5 | 6 | 7 |

604

| Storage | -, 0 | | | | | | | |
|---|---|---|---|---|---|---|---|---|
| Sample | C | A | B | D | E | - | - | - |
| Position | 0 | 1 | 2 | 3 | 4 | 5 | 6 | 7 |

| Storage | | | | | | | | | |
|---|---|---|---|---|---|---|---|---|---|
| Sample | A | B | C | D | S | - | - | - | - |
| Position | Probe | 1 | 2 | 3 | 4 | 5 | 6 | 7 | 8 |

612

| Storage | | | | | S | | | | |
|---|---|---|---|---|---|---|---|---|---|
| Sample | A | B | C | D | - | - | - | - | - |
| Position | Probe | 1 | 2 | 3 | 4 | 5 | 6 | 7 | 8 |

613

| Storage | | | | | S | | | | |
|---|---|---|---|---|---|---|---|---|---|
| Sample | - | - | - | - | - | B | C | D | - |
| Position | Probe | 1 | 2 | 3 | 4 | 5 | 6 | 7 | 8 |

614

| Storage | | | | | - | | | | |
|---|---|---|---|---|---|---|---|---|---|
| Sample | S | B | C | D | - | - | - | - | - |
| Position | Probe | 1 | 2 | 3 | 4 | 5 | 6 | 7 | 8 |

FIG. 14

| Storage/ Probe | | | | | A | | | | |
|---|---|---|---|---|---|---|---|---|---|
| Sample | - | - | - | - | - | B | C | D | S |
| Position | Egress | 1 | 2 | 3 | 4 | 5 | 6 | 7 | 8 |

621

| Storage/ Probe | | | | | S | | | | |
|---|---|---|---|---|---|---|---|---|---|
| Sample | A | B | C | D | - | - | - | - | - |
| Position | Egress | 1 | 2 | 3 | 4 | 5 | 6 | 7 | 8 |

622

| Storage/ Probe | | | | | - | | | | |
|---|---|---|---|---|---|---|---|---|---|
| Sample | S | - | - | - | - | B | C | D | - |
| Position | Egress | 1 | 2 | 3 | 4 | 5 | 6 | 7 | 8 |

| Position | 0 | 1 | 2 | 3 | 4 | 5 | 6 | 7 |
|---|---|---|---|---|---|---|---|---|
| Sample | - | - | - | A | B | C | D | E |
| Probe | | | | | | | | |
| Storage | | | | | | | | |

632

| Position | 0 | 1 | 2 | 3 | 4 | 5 | 6 | 7 |
|---|---|---|---|---|---|---|---|---|
| Sample | - | - | B | C | D | - | - | - |
| Probe | | | A | | | | | |
| Storage | | | | | | E | | |

633

| Position | 0 | 1 | 2 | 3 | 4 | 5 | 6 | 7 |
|---|---|---|---|---|---|---|---|---|
| Sample | - | - | - | - | B | E | C | D |
| Probe | | | A | | | | | |
| Storage | | | | | | - | | |

FIG. 16A

| Storage | | | | | | - | | |
|---|---|---|---|---|---|---|---|---|
| Probe | | | E | | | | | |
| Sample | - | B | - | C | D | - | - | - |
| Position | 0 | 1 | 2 | 3 | 4 | 5 | 6 | 7 |

LINEAR RANDOM ACCESS QUEUE

CROSS-REFERENCE TO RELATED APPLICATIONS

This application claims priority to U.S. provisional application Ser. No. 61/650,015 filed May 22, 2012, which is incorporated herein by reference in its entirety.

TECHNOLOGY FIELD

The present invention relates in general to an automation system for use in a laboratory environment and, more particularly, to systems and methods for transporting patient samples for in vitro diagnostics (IVD) in a clinical analyzer via active transport devices. Embodiments of the present invention are particularly well suited for, but in no way limited to, methods and apparatus for maintaining sample queues in a bidirectional track in an IVD automation system.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples have been loaded. The analyzer extracts a liquid sample from the vial and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer) which may include immunoassay (IA) and clinical chemistry (CC) stations. Some traditional IVD automation track systems comprise systems that are designated to transport samples from one fully independent module to another standalone module. This allows different types of tests to be specialized in two different stations or allows two redundant stations to be linked to increase the volume of sample throughput available. These lab automation systems, however, are often bottlenecks in multi-station analyzers. Relatively speaking, traditional lab automation systems lack large degrees of intelligence or autonomy to allow samples to independently move between stations.

In an exemplary prior art system, a friction track, much like a conveyor belt, shuttles individual carrier mechanisms, sometimes called pucks, or racks of containers between different stations. Samples may be stored in sample containers, such as in test tubes that are placed into a puck by an operator or robot arm for transport between stations in an analyzer along the track. This friction track, however, can only move in one direction at a time and any samples on the track will move in the same direction at the same speed. When a sample needs to exit the friction track, gating/switching can be used to move individual pucks into offshoot paths (sometimes called sidecars or pullouts). A drawback with this set-up is that singulation must be used to control the direction of any given puck at each gate and switch. For example, if two pucks are near one another and only one puck should be redirected into an offshoot path, it becomes difficult to control a switch so that only one puck is moved into the offshoot path and ensure that the proper puck is pulled from the friction track. This has created the need in many prior art systems to have pucks stop at a gate so that individual pucks can be released and switched one at a time at each decision point on a track. Because the transition between main tracks and sidecar/pullout tracks is slow, queues can build up at decision points at the junction of the main track and sidecar, in addition to the queues that build up on sidecar/pullout tracks.

Traditional linear tracks lack precision or intelligence for providing intelligent transport queuing. While a traditional linear track may be suitable for handling samples on a first-in-first-out (FIFO) basis, other mechanisms are needed to handle samples if random access is needed. For example, carousels may be used to selectively interact with samples in a ring. By rotating the ring, an arbitrary sample can be selected. However, the carousel approach has certain drawbacks. The needed space requirements grow as the square of the number of samples a carousel can hold, and it requires a large round area. Furthermore, carousels may require slow mechanisms to load and unload a sample from a carousel. In addition, the centrifugal forces applied to samples in a carousel can limit the speed at which a carousel operates.

Another drawback of sample queues in prior art tracks is that they may encounter problems when a STAT sample arrives. Even if FIFO access is satisfactory for non-STAT samples, when a STAT sample arrives, a queue may need to be flushed so that a STAT sample can immediately be handled. Any samples in the queue will generally be dumped from a queue to the main track, where they may encounter traffic and high latency from queues at singulation points on the track, as the dumped samples have to traverse the main track to return to the sidecar from which they were dumped.

SUMMARY

Embodiments of the present invention address and overcome one or more of the above shortcomings and drawbacks by providing devices and systems for providing location information and trajectory information for use by intelligent carriers that transport samples. This technology is particularly well-suited for, but by no means limited to, transport mechanisms in an automation system for use in an in vitro diagnostics (IVD) environment.

Embodiments of the present invention are directed to methods and systems for managing queues of sample carriers in a bidirectional track. The queues can behave as linear FIFO queues or can be resorted to provide random access to samples in the queue using one or more storage positions to allow sample carriers to be selectively removed and reinserted into the queue, allowing the order of sample carriers to be resorted.

According to one embodiment of the invention, an automation system for use with an automated clinical analyzer includes a bidirectional track and a plurality of sample carriers configured to move along the bidirectional track. At least one storage location is accessible to the bidirectional track. A processor is configured to sort the plurality of sample carriers by directing the carriers along the bidirectional track, and by directing at least one sample carrier into and out of the storage location to change the order of carriers with respect to the bidirectional track.

According to one aspect of the invention, at least one location of the bidirectional track is accessible to a pipette.

According to another aspect of the invention, the storage location is configured to allow a pipette to interact with a sample carried by the at least one sample carrier. In another aspect, the processor is configured to use an insertion sort algorithm or a heapsort algorithm to sort the plurality of sample carriers. In yet another aspect, at least one storage location comprises multiple storage locations spaced apart along the bidirectional track. In still another aspect, the processor is configured to use the multiple storage locations to sort a queue of sample carriers that is longer than the distance between two adjacent storage locations.

According to one aspect of the invention, the processor is configured to use the multiple storage locations to sort a queue of sample carriers that is longer than the distance between at least one storage location and an end of the bidirectional track. According to another aspect of the invention, at least one storage location is configured to store more than one of the plurality of sample carriers simultaneously. In another aspect, at least one storage location comprises a track section that is perpendicular to the bidirectional track. In another aspect, at least one storage location comprises a storage area that is accessible to the bidirectional track via at least one curved section of track.

According to one aspect of the invention, the bidirectional track comprises a friction track. In yet another aspect, the bidirectional track comprises a track section having electromagnetic coils to move each sample carrier. In still another aspect, the plurality of the sample carriers are configured to be independently movable.

According to another embodiment of the invention, a method for use with an automation system for use with an automated clinical analyzer includes the steps of determining (using at least one processor) an order of sample aspiration for a plurality of samples in a queue on a bidirectional track, identifying at least one first sample in the queue that is out of order, and causing (via at least one electrical signal) the first sample to move along the bidirectional track to a physical location on the bidirectional track accessible to a first storage location. The first sample is moved into the first storage location and at least a subset of the plurality of samples is caused to move, via at least one electrical signal, such that a gap in the plurality of samples exists at a first predetermined ordinal position in the queue coincident with a location accessible to the first storage location. The first sample is then moved out of the first storage location into the predetermined ordinal position.

According to one aspect of the invention, a volume of the first sample is aspirated while it is in the first storage location. According to another aspect of the invention, a volume of the first sample is aspirated while it is on the bidirectional track. In another aspect, the step of identifying the first sample is performed by at least one processor executing an insertion sort algorithm or a heapsort algorithm, for example.

In yet another aspect, the method includes steps of identifying a second sample in the queue that is out of order, causing, via at least one electrical signal, the second sample to move along the bidirectional track to a physical location on the bidirectional track accessible to a second storage location, and moving the second sample into the second storage location. The method further causes (via at least one electrical signal) at least a subset of the plurality of samples to move such that a gap in the plurality of samples exists at a second predetermined ordinal position in the queue coincident with a location accessible to the second storage location, and moves the second sample out of the second storage location into the second predetermined ordinal position.

According to one aspect of the invention, the step of determining the order of sample aspiration includes considering a plurality of priorities of the samples. According to another aspect of the invention, the step of identifying at least one first sample in the queue that is out of order comprises identifying a STAT sample that is not at the head of the queue.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 13 illustrates states within a sample queue that may be encountered when using embodiments of the present invention;

FIG. 14 illustrates states within a sample queue that may be encountered when using embodiments of the present invention;

FIG. 15 illustrates states within an exemplary track that may be encountered when using embodiments of the present invention;

FIGS. 16A-B illustrate states within an exemplary track that may be encountered when using embodiments of the present invention;

DETAILED DESCRIPTION OF ILLUSTRATIVE EMBODIMENTS

Figure 1:
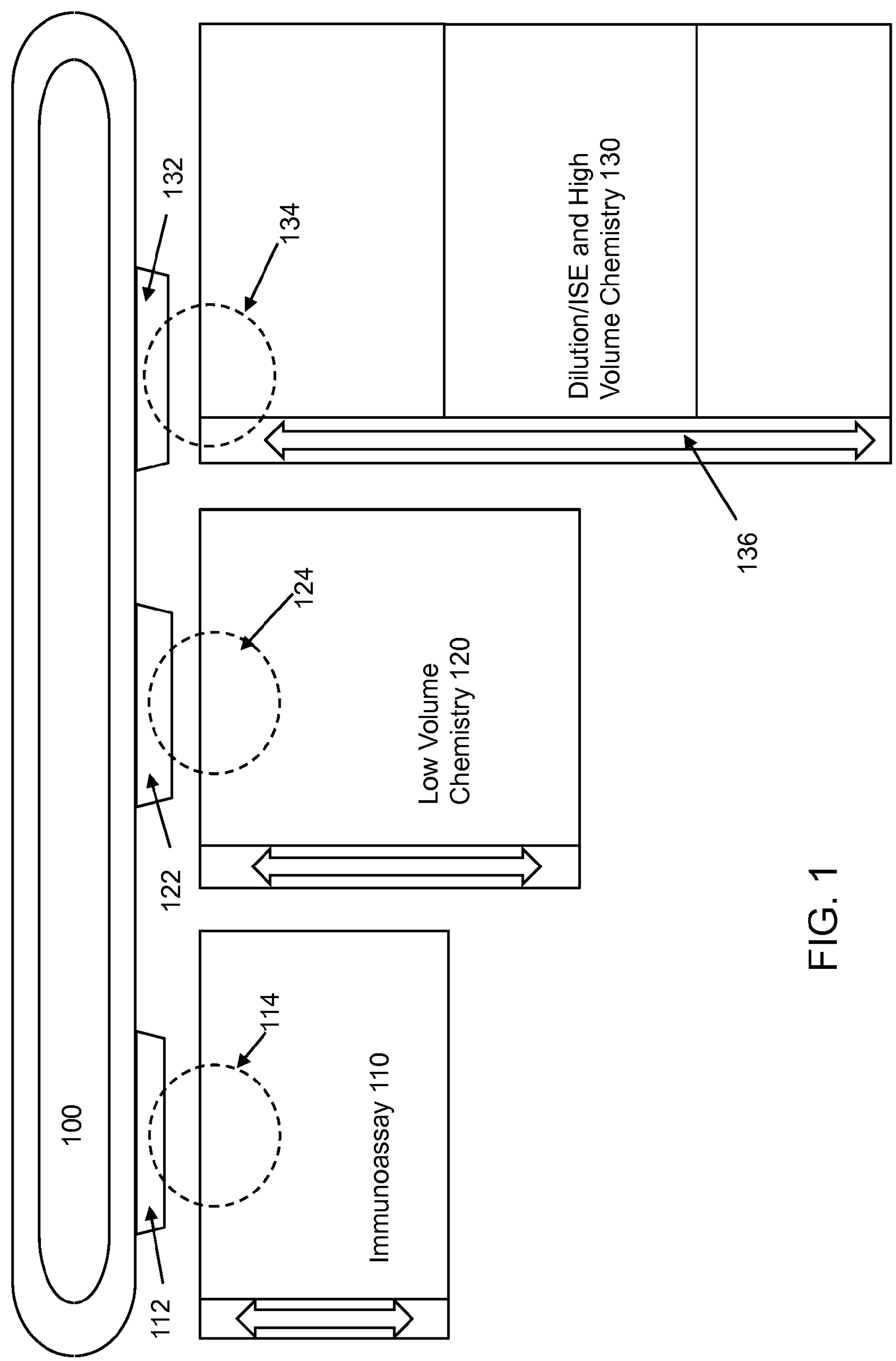
FIG. 1 is a top view of an exemplary clinical chemistry analyzer geometry that can be improved by use of the automation system embodiments disclosed.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes; maximum jerk, acceleration, direction, and/or speed for the carrier while moving in the automation system. The motion profile can limit or define the trajectory for each carrier independently. In some embodiments, a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. WD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Exemplary Embodiments

Some of the problems in the prior art may be resolved or addressed by utilizing some of the exemplary improved apparatus and methods for handling queues within an automated clinical chemistry analyzer (analyzer) disclosed herein. Specifically, by providing storage positions adjacent to tracks containing sample carriers, an otherwise FIFO queue can also be used to provide random access to samples. Because the tracks used for moving samples also hold the samples contained in the queue, the space needed to handle samples can be reduced over certain prior art mechanisms. Specifically, the amount of track space needed for a queue is directly proportional to the number of samples within the queue. Prior art mechanisms implementing random access queues using carousel type devices require more space, because the amount of space needed grows as the square of the number of samples contained in the queue. Furthermore, because the track is already used to transport samples, the additional space needed for handling queues can be de minimis. The track holding the queue can be any suitable track section, including a track section serving as a main track or a side track, such as a sidecar/pullout.

An exemplary track geometry for use in transporting samples within an analyzer, typical in prior art configurations, is shown in FIG. 1. This track can include prior art friction tracks, which may introduce problems in designing a track system. However, certain embodiments of the present invention could also use a similar geometry without necessarily employing a friction track for motion. Track 100 can be a generally oval-shaped track that conveys samples in pucks or trays between various stations, such as sample preparation stations, or analyzing/testing stations 110, 120, and 130. Track 100 could be a single direction track or, in some instances, a linear bidirectional track. In this exemplary set-up, each analyzer 110, 120, 130 is serviced by a respective sidecar 112, 122, 132. At the junction between the track 100 and each sidecar, a gate or switch can be placed that allows samples to be diverted to or from track 100 to the sidecar. The oval nature of track 100 can be used to circulate samples while they wait for access to each analyzer. For example, analyzer 110 may have a full queue in sidecar 112, such that new samples on track 100 cannot be diverted to pullout 112 until analyzer 110 finishes handling a pending sample in sidecar 112 and inserts it back into the main traffic flow of track 100.

In some prior art systems, each sidecar can be serviced by a handling mechanism such as sample probe arms 114, 124, and 134. These robotic handling arms can aspirate sample material from samples on a sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry station (or stations) 130. Some advantages of this approach are that the track 100 can be part of a separate lab automation system that can be added onto otherwise self-contained stations, and the track 100 and stations 110, 120, and 130 can be independently upgraded, purchased, or serviced. Some stations, such as high-volume chemistry station 130, can include their own friction track 136 that operates independently of track 100. Friction track 136 can include a bidirectional friction track that allows samples to move between sub-modules of high-volume chemistry station 130. A drawback of this type of system is that the separate friction tracks operate independently and control of overall automation becomes more complicated. Furthermore, transitions between friction tracks 136 and 100 can be slow and cumbersome, particularly where there is no direct route between two friction tracks. In some systems, moving between tracks may require lifting and placing samples via a robot arm.

Prior art lab automation systems for analyzers generally treat individual analyzer testing stations as generic destinations for a sample on the track. In some embodiments of the present invention, the lab automation system can be integrated within the individual testing stations, which can substantially reduce or eliminate the complexity of the individual testing stations and reduce the need for separate sample handling systems within each station. In some embodiments, by integrating the lab automation system into the stations, the system can begin to treat individual stations less as generic destinations and more as portions of a multi-route track onto which a sample can travel.

Figure 2A:
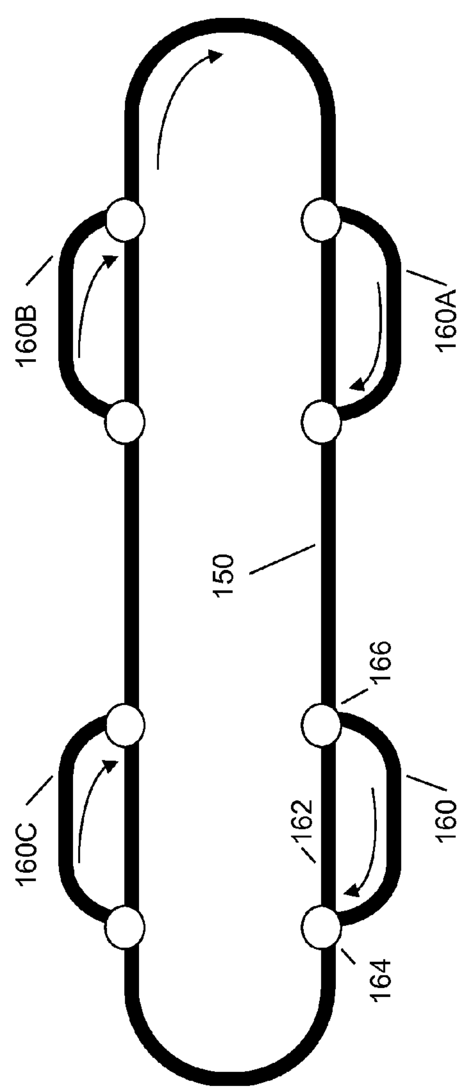
FIGS. 2A and 2B are diagrammatic views of track geometries that can be used with the automation system embodiments disclosed herein.

FIG. 2A shows one embodiment of a track system that can be adapted for use with the present invention. Track 150 is a rectangular/oval/circular track on which sample carriers move in a clockwise (or counterclockwise) direction. Track 150 may be unidirectional or bidirectional. Carriers can transport any suitable payload within an IVD environment, such as fluid samples, reagents or waste. Fluids, such as patient samples, can be placed in a container or vessel, such as a test tube, vial, cuvette, etc., that can be transported by a carrier. Carriers and, by extension, payloads such as samples, can move on the main track 150 or be diverted via decision points such as 164 or 166. These decision points can be mechanical gates (as in the prior art) or other mechanisms suitable for allowing a sample to be diverted from the main track 150 to a sidecar, such as 160, 160A, 160B, 160C as described herein. By way of example, if a sample carrier is traversing the main path 150 and reaches decision point 166, it can be made to continue on the main track to segment 162, or it can be made to divert to sidecar 160. The systems and methods by which the decision can be made to divert the sample carrier at decision point 166 are described throughout.

Figure 2B:
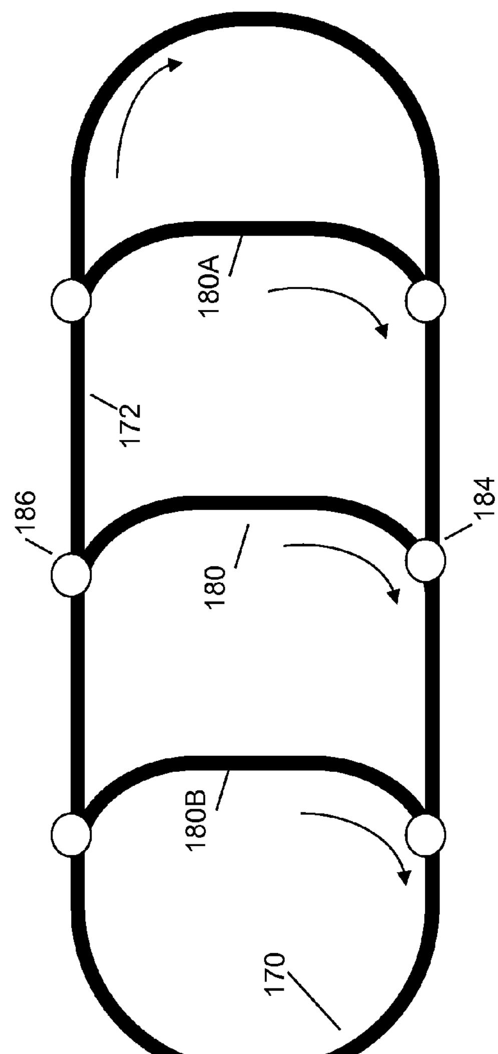

FIG. 2B shows an alternative track layout that may be suitable for certain embodiments of the present invention. Track 170 is also a generally circular track with sample carriers moving clockwise (or counterclockwise). In this example, rather than having sidecars outside of the track, pullouts 180, 180A, and 180B are chords within the track. Similarly, when sample carriers reach decision points, they may be diverted off of the main path to a side path such as path 180. At decision point 186, a sample on the main track 170 can be made to continue on the main track or be diverted onto path 180. Once an analyzer station along handling path 180 is done processing the sample, the sample proceeds to decision point 184 where it may be placed back onto the main path 170.

Figure 3:
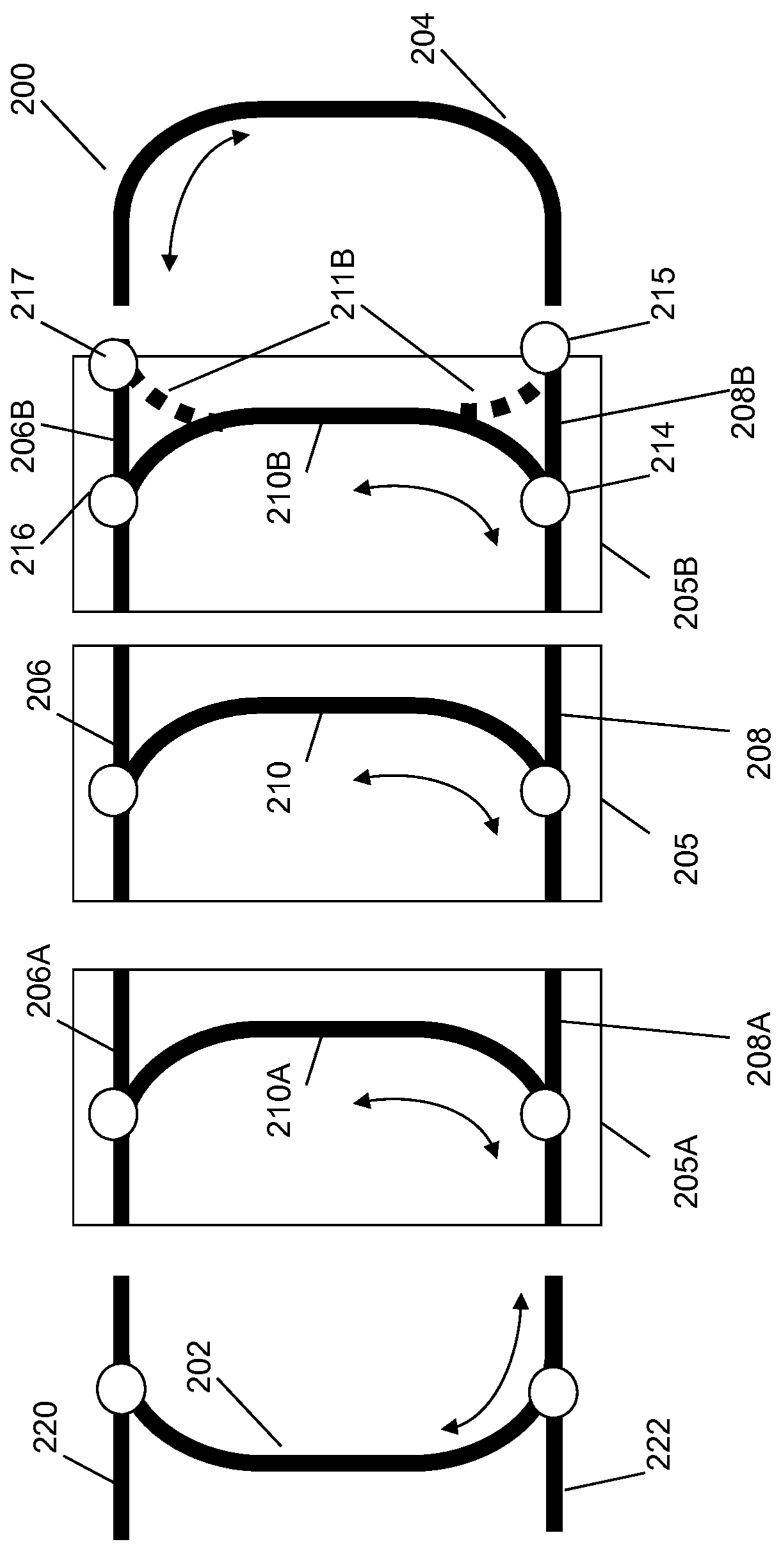
FIG. 3 is a diagrammatic view of an exemplary modular track configuration that can be used with the embodiments disclosed herein.

FIG. 3 shows a modular approach to the automation system track that can be used for certain embodiments of the present invention. In this example, the tracks may be integrated into individual analyzer stations such that the track can be used as part of the internal motion or sample handling system of individual lab stations. In the prior art, it is common to have multiple different types of motion systems within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed. In some embodiments, by integrating portions of the track system into the analyzer stations themselves, each station can include its own queuing logic and may be simplified to eliminate unnecessary internal motion systems.

With respect to FIG. 3, the track 200 can be broken into modular components that are integrated into analyzer modules. In this exemplary track, modules 205, 205A, and 205B can be combined with one another and optionally other modular track components 202 and 204 to form a track similar to that shown in FIG. 2B. For instance, 205A can be a module that performs the same function as immunoassay 110 (FIG. 1), 205 can be a module that performs the same function as low-volume chemistry module 120 (FIG. 1), and 205B can be a module that performs ISE electrolyte testing, like module 130 (FIG. 1). In this example, the main outer track can be formed by track segments 202, 204, 206, 206A, 206B, 208, 208A, and 208B. Within the analyzer modules 205, 205A, and 205B, internal paths 210, 210A, and 210B form pullouts from the main track. The internal paths can be used for internal queuing and can be managed independently within each analyzer module to allow each module to have greater control over samples to be processed.

One advantage of integrating track 200 and subpaths 210, 210A, and 210B into the analyzer modules 205, 205A, and 205B, respectively, is that the internal handling mechanisms within each analyzer module can be specially adapted to better coordinate with the track subpaths. In some embodiments, modules 205, 205A, and 205B can be adapted to process each sample within a period that is less than an operation cycle of the overall analyzer, leaving enough time for the sample to be routed along the track system to another module after processing, allowing the other module to immediately process the sample on the next operation cycle. As used herein, an operation cycle is a unit of time used by scheduling algorithms to allot processing time to modules for sample assays. These can be dynamic or fixed and can allow synchronous operation of the modules in the analyzer and provide a reliable timing model for scheduling samples amongst multiple modules in the analyzer. The operation cycle time can be chosen to be the time needed by any given module between when it starts processing a first sample, and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle, to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle times or demand vary between modules.

Enabling transit between modules in the analyzer in a reliable time frame, on the order of a single operation cycle or less, achieves many performance advantages not possible with prior art track systems. If a sample can be reliably handled by an analyzer module and transported to the next analyzer module within a single cycle of the analyzer, traffic handling in queuing becomes much simpler, throughput becomes more consistent, and latency can be controlled and reduced. Essentially, in such an analyzer, a sample can reliably be handled by the track system and processed uniformly such that a sample does not sit idly on the track system waiting in queues. Furthermore, queues within the system, such as queues within a given analyzer module, can reliably be shortened, limited by the number of modules within the system.

In some embodiments of the present invention, the reliable and rapid nature of the track system enables queues to be virtual, rather than physical. A virtual queue can be handled in software, rather than by physical limitations. Traditionally, queues have been physical. The simplest physical queue is effectively a traffic jam at any given part of a sample handling operation. A bottleneck creates a first-in first-out (FIFO) queue, where sample carriers are effectively stopped in a line, providing a buffer so that an analyzer or a decision point can request the next sample in the queue when it is ready. Most prior art lab automation tracks maintain FIFO processing queues to buffer samples that are waiting to be processed by the attached modules (analyzers or pre/post analytic devices). These buffers allow the track to process sample tubes at a constant rate, even though the modules or operator requests can create bursts of demand. FIFO queues can also substantially increase the throughput of the individual modules by allowing them to perform preprocessing tasks for future samples, for example, prepare a cuvette or aspirate reagent, while processing the current sample. While the rigid predictability of FIFO queues enables the parallelization of some processing tasks, it also can prevent the modules from using opportunistic scheduling that may increase throughput by reordering tests on samples to optimize resources. For example, the internal resource conflicts of most immunoassay analyzers can be so complex that the analyzers need to interleave the tests from multiple samples in order to reach maximum efficiency. A FIFO queue can reduce the throughput of these analyzers by as much as 20%. Another challenge with FIFO queues is their inability to handle priority samples (e.g., a STAT sample). If a STAT sample needs to be processed immediately, the entire FIFO queue has to be flushed back onto the main track, delaying all other samples on the track and forcing the original module to slowly rebuild its queue.

Another type of queue is a random access (RA) queue. A carousel is an example of a physical random access (RA) queue found in analyzer modules. By aliquoting a portion of a sample into one or more vessels in a carousel ring, an analyzer module can select any of a number of samples to process at any time within the analyzer. However, carousels have many drawbacks, including added complexity, size, and cost. A carousel also increases the steady-state processing time, because a sample must be transferred into and out of the random-access queue. Processing delays depend on the implementation, such as the number of positions in a carousel. On the other hand, by having random access to samples, a local scheduling mechanism within a module can process samples in parallel, performing sub-steps in any order it desires.

In some embodiments, carousels or other RA queues can be eliminated from the modules and the subpaths (e.g., 210)

from the automation system can be used as part of an RA or FIFO queue. That is, if the travel time for a sample between any two points can be bounded to a known time that is similar to that of a carousel (such as predictably less than a portion of an operation cycle), the track 200 can be part of the queue for a given module. For example, rather than using a carousel, module 205 can utilize samples in carriers on subpath 210. Preprocessing steps, such as reagent preparation, can be conducted prior to the arrival of a sample under test. Once that sample under test arrives, one or more portions of the sample can be aspirated into cuvettes or other reaction vessels for an assay. In some embodiments, these reaction vessels can be contained within module 205, off track, while in other embodiments, these reaction vessels can be placed in carriers on subpath 210 to allow easy motion. If the sample under test is required to be at a module for longer than an operation cycle, or if multiple samples will be processed by the module during an operation cycle, the subpath 210 can act as a queue for the module.

Furthermore, samples not yet under test, which may be currently located at other modules, can be scheduled for the next operation cycle. These next-cycle samples can be considered as residing in a virtual queue for module 205. A module can schedule samples to arrive during a given operation cycle for any sample on track 200. A central controller, or controllers associated with modules themselves, can resolve any conflicts over a sample for a given cycle. By giving a module prior knowledge of the arrival time of a sample, each module can prepare resources and interleave tests or portions of tests to more efficiently allot internal resources. In this manner, modules can operate on samples in a just-in-time manner, rather than by using large physical buffers. The effect is that the virtual queue for a given module can be much larger than the physical capacity of the subpath serving that module, and existing scheduling algorithms can be used. Effectively, each module can treat track 200 as it would treat a sample carousel in a prior art module.

It should be appreciated that by employing virtual queues, in some embodiments, multiple modules can have multiple queues and can share a single queue or samples within a queue. For example, if two modules are equipped to perform a certain assay, a sample needing that assay can be assigned to a virtual queue for that assay, which is shared between the two modules capable of handling the assay. This allows load balancing between modules and can facilitate parallelism. In embodiments where reaction vessels are placed in carriers on track 200, an assay can be started at one module (e.g., reagents prepared and/or sample mixed in) and the assay can be completed at another (e.g., a reaction is observed at another module). Multiple modules can effectively be thought of as a multi-core processor for handling samples in some embodiments. In these embodiments, scheduling algorithms for the multiple modules should be coordinated to avoid conflicts for samples during a given operation cycle.

By employing virtual queues, modules can operate on samples while the samples are in the virtual queues of other modules. This allows low latency of samples, as each sample that is placed onto track 200 can be processed as quickly as the modules can complete the tests, without having to wait through a physical queue. This can greatly reduce the number of sample carriers on track 200 at any given time, allowing reliable throughput. By allowing modules to share queues or samples, load balancing can also be used to maximize throughput of the system.

Another advantage of using virtual queues is that STAT samples can be dynamically assigned priority. For example, a STAT sample can be moved to the head of any queue for the next operation cycle in software, rather than having to use a physical bypass to leapfrog a STAT sample to the head of a largely static physical queue. For example, if a module is expecting three samples to be delivered by track 200 for assays during the next operation cycle, a scheduler responsible for assigning samples to the module can simply replace one or more of the samples with the STAT sample, and have the track 200 deliver the STAT sample for processing during the next operation cycle.

While virtual queues can be used in some embodiments, some embodiments use physical queues for at least part of an analyzer. For example, a subpath serving a pipette for an analyzer may still have a physical queue on that subpath, as samples wait to interact with the pipette. Management of this queue can include virtualization and can also include using the track of the subpath as a physical buffer. This physical buffer can comprise a FIFO queue and, as explained herein, can also be operated in a random access manner by using storage locations accessible to the track that holds the queue. This virtualization of queues can be helpful for managing the interaction of samples between modules. However, physical buffers on certain track sections may still be employed to allow physical management of samples within the analyzer. By using track sections as physical queues, these physical queues can be managed as part of a larger virtual queue without requiring added storage space for the samples. By using physical queues, the track can act as a transportation mechanism for samples, as well as physical storage for the samples when not being aspirated via a pipette.

If decision points such as 214 and 216 can be streamlined such that there is no need for a queue at each decision point, the only physical queues can be within subpaths 210, 210A, and 210B. As described above, these can be treated as RA queues or FIFO queues. If a STAT sample is placed onto track 200, RA queues within subpaths 210, 210A, and 210B need not be flushed, as the STAT sample can be processed immediately. Any FIFO queues can be individually flushed. For example, if a STAT sample is placed onto track 200 at section 222, the sample may be routed to the appropriate analyzer 205B via the outside track and decision point 216. If there are other samples (and, by extension, the sample carriers transporting those samples) waiting in the queue in path 210B, only those samples in the queue may need to be flushed to allow the STAT sample to take priority. If the outer track 200 is presumed to take less than an operation cycle to traverse, any samples that were flushed from the queue in 210B can simply be circulated around the track and placed immediately back into the queue in path 210B immediately behind the STAT sample, eliminating any down time caused by the STAT sample.

Entry paths 220 and 222 can be used to input samples to the track 200. For example, regular priority samples can be placed onto track 200 at input 220 and STAT priority samples can be placed on input 222. These inputs can be used as outputs for samples when complete, or other ports (not shown) can be used as the output paths for used samples. Input 220 can be implemented as an input buffer, acting as a FIFO queue for input samples seeking access to the track 200. Once a sample reaches the head of the queue at input 220, it can be moved onto the track (either by being placed in a carrier or by being placed in a carrier when it is placed in input 220). A STAT sample can enter the track 200 immediately after being placed at input 222 or, if track 200 is overcrowded, the STAT sample can enter the track at the next available uncrowded operation cycle. Some embodiments monitor the number of carriers on the track during an operation cycle and limit the total number to a manageable amount, leaving the remainder in input queues. By restricting samples at the input, track 200 can be free of traffic, allowing it to always be operated in the most efficient manner possible. In these embodiments, the transit time of a sample between two modules can be a bounded value (e.g., less than some portion of an operation cycle), allowing simplified scheduling.

In some embodiments, the track system 200 can be designed to be bidirectional. This means that sample carriers can traverse the outside path and/or any subpaths in either direction. In some embodiments, additional subpaths, such as 211B accessed via additional decision points 215 and 217, can assist in providing bidirectional access. Bidirectional paths can have inherent advantages. For example, if normal priority samples are always handled in the same direction, a STAT sample can be handled in the opposite direction along the subpath. This means that a STAT sample can essentially enter the exit of the subpath and be immediately placed at the head of the queue without requiring the queue to be flushed. For example, if a STAT sample is placed on track 200 at segment 204, it can enter path 210B via decision point 214 and proceed into path 210B to be immediately placed at the head of any queue. Meanwhile, in all of these examples, because queues are presumed to be limited generally to subpaths, there is no need to flush queues in other modules if a STAT sample does not need immediate access to those modules. Any additional modules that need to service a STAT sample on a subsequent cycle can flush their queues at that point, providing just-in-time access to a STAT sample without otherwise disrupting the operation of each analyzer module.

Modular design also allows certain other advantages. If the automation systems within an analyzer module are adapted to take advantage of the track system contained in the module, new features can be added that use the common track. For example, a module could have its own internal reagent carousel that includes all of the reagents necessary for performing the assays prescribed for the samples. When reagents stocked in the analyzer module run low, an operator can replenish the reagents in some embodiments by simply loading additional reagents onto carriers on the track 200. When the reagents on track 200 reach the appropriate module, the module can utilize mechanical systems such as an arm or a feeder system that takes the reagents off of the track and places the reagents in the reagents store for the module.

In some embodiments, the individual track portions shown in FIG. 3 and FIG. 2A and FIG. 2B can be operated independently from one another, or can be passive. Independent carrier movement provides advantages over friction-based track systems, such as non-localized conveyor belts where the entire friction track must be moved to effect movement of a sample carrier. This means that other samples also on that track must move at the same rate. This also means that, if certain sections operate at different speeds, collisions between passive carriers carrying samples can occur.

Figure 4A:
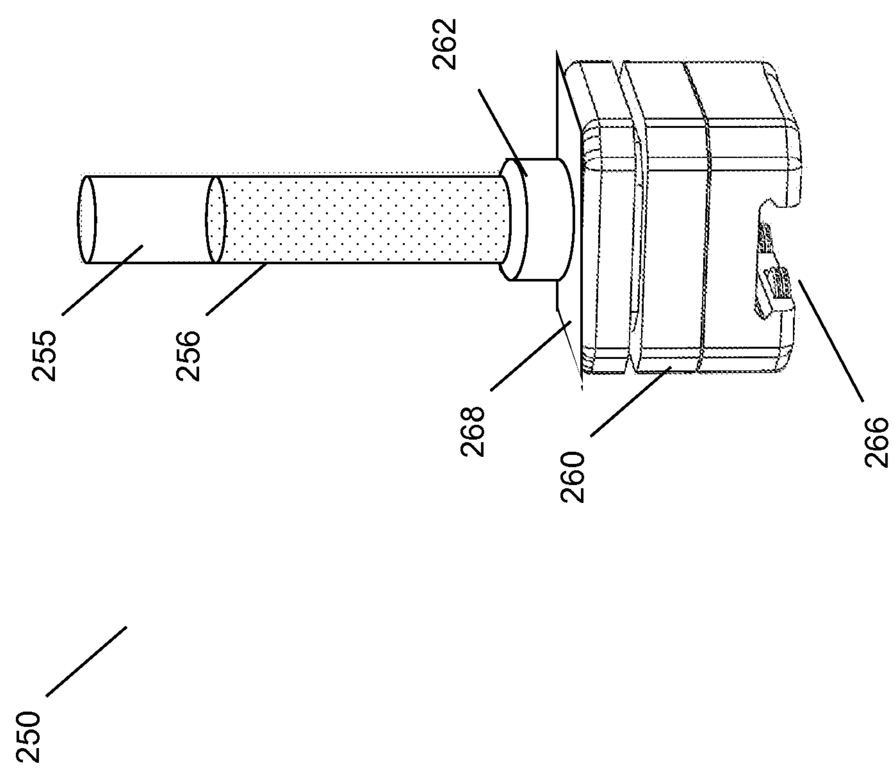
FIG. 4A is a perspective view of an exemplary carrier that can be used with the embodiments disclosed herein.

FIG. 4A depicts an exemplary carrier 250 for use with the present invention. Carrier 250 can hold different payloads in different embodiments. One payload can be a sample tube 255, which contains a fluid sample 256, such as blood or urine. Other payloads may include racks of tubes or reagent cartridges, or any other suitable cartridge. Sample carrier 250 includes a main housing body 260, which can house the internal electronic components described herein. The main housing 260 supports a bracket 262, which can accept a payload. In some embodiments, this is a shallow hole that is designed to accept a fluid container 255, such as a sample tube, and hold it with a friction fit. In some embodiments, the friction fit can be made using an elastic bore or a clamp that can be fixed or energized with a spring to create a holding force. In some embodiments, sample racks and reagent cartridges can be designed to also attach to the bracket 262, allowing bracket 262 to act as a universal base for multiple payload types.

Body 260 can include, or be coupled to, guide portion 266, which allows the carrier 250 to follow a track between decision points. Guide portion 266 can include, for example, a slot to accept one or more rails in the track, providing lateral and/or vertical support. In some embodiments, the guide portion 266 allows the carrier 250 to be guided by walls in the track, such as the walls of a trough-shaped track. The guide portion 266 can also include drive mechanisms, such as friction wheels that allow a motor in the carrier body 260 to drive the carrier or puck 250 forward or backward on the track. The guide portion 266 can include other drive components suitable for use with the embodiments described throughout, such as magnets or induction coils. In some embodiments, the guide portion 266 can be physically constrained by the track, such that the range of motion is substantially bidirectional within the track and one-dimensional within the reference frame of the track (i.e., the motion is restricted transversely so that the carrier 250 can only move forward or backward along the track, even though the track may itself be two or three-dimensional.) In some embodiments, the guide portion 266 can be less constrained laterally (e.g., more like a car on a road than a train on a track), such that the carrier 250 can control its lateral position, such as via a steering mechanism. In these embodiments, a carrier 250 can vary its position in two dimensions relative to the track. Embodiments of two-dimensional position marks can be useful for facilitating the positioning of a carrier 250 in one or two dimensions.

Rewritable display 268 can be provided on the top of the carrier 250. This display can include an LCD oriented panel and can be updated in real time by the carrier 250 to display status information about sample 256. By providing the electronically rewritable display on the top of the carrier 250, the status information can be viewed at a glance by an operator. This can allow an operator to quickly determine which sample he/she is looking for when there are multiple carriers 250 in a group. By placing the rewritable display on top of the carrier 250, an operator can determine status information even when multiple carriers 250 are in a drawer or rack.

Figure 4B:
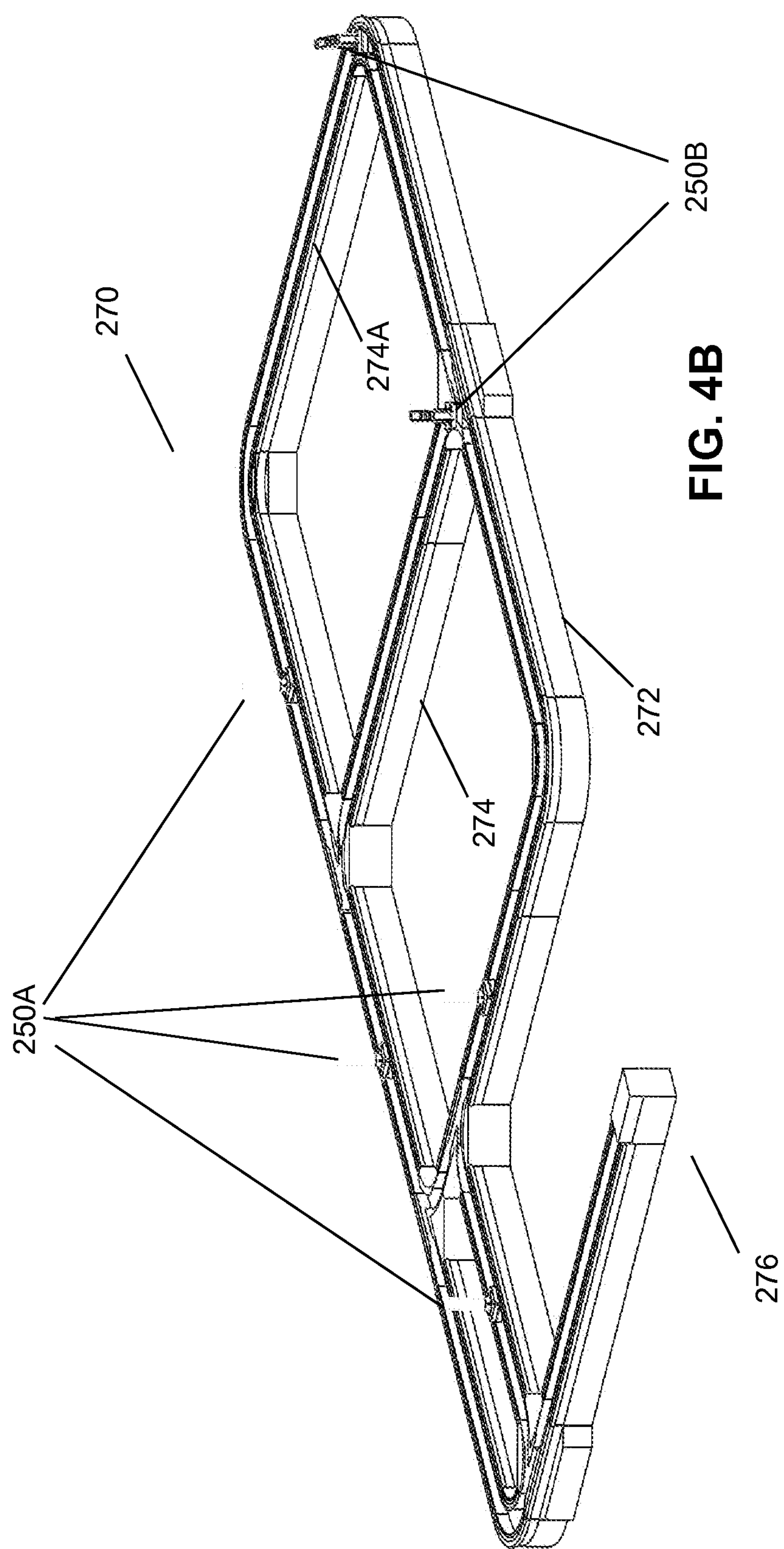
FIG. 4B is a perspective view of an exemplary track configuration that can be used with the embodiments disclosed herein.

FIG. 4B shows an exemplary track configuration 270 for use by carriers 250A. In this example, carriers 250A transport sample tubes, while carriers 250B transport racks of tubes along main track 272 and/or subpaths 274 and 274A. Path 276 can be used by an operator to place samples into carriers or remove samples from these carriers.

Figure 4C:
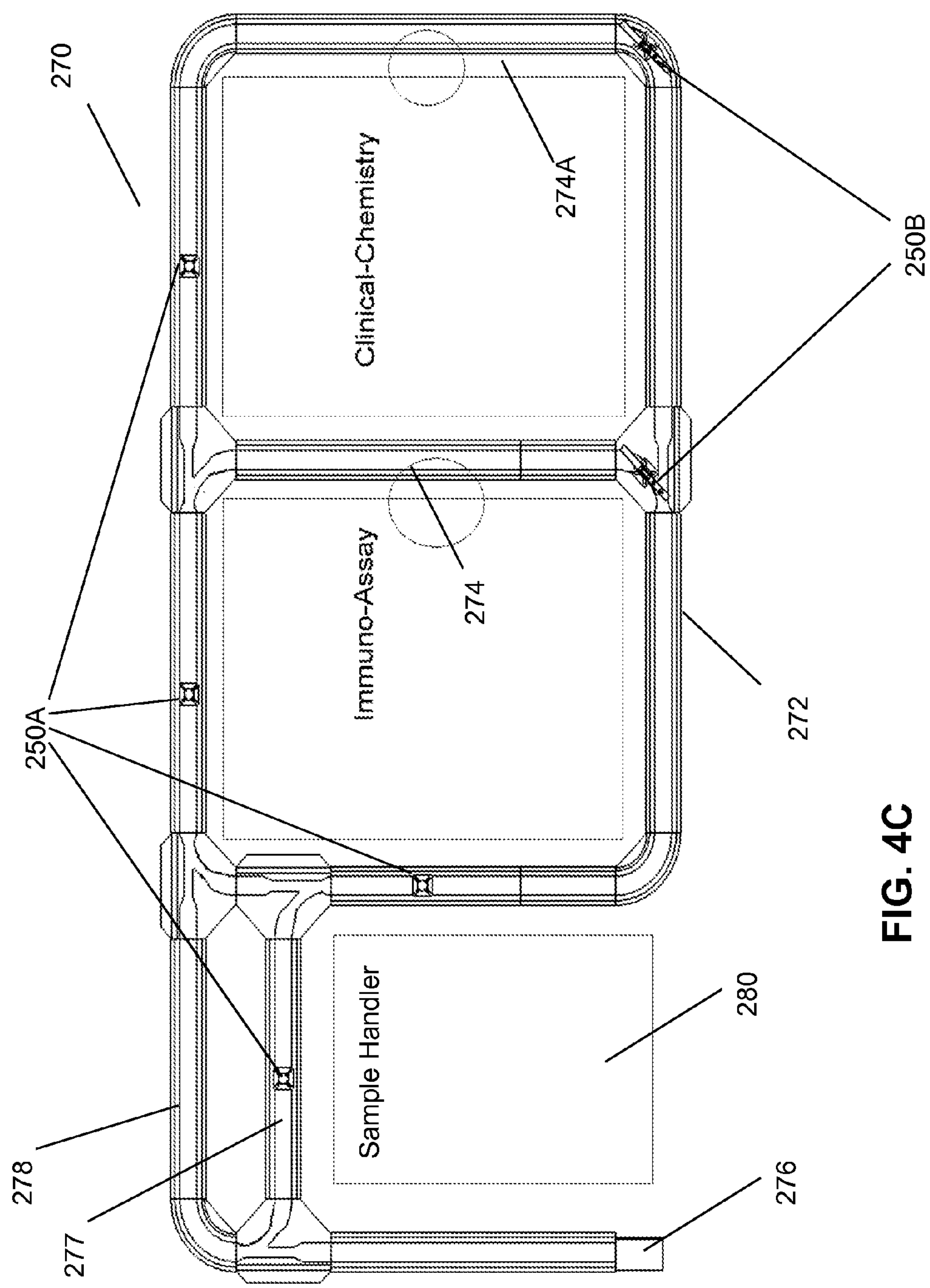
FIG. 4C is a top view of an exemplary track configuration that can be used with the embodiments disclosed herein.

FIG. 4C shows an additional view of an exemplary track configuration 270. In this example, subpath 274 serves an immunoassay station, while subpath 274A serves a clinical chemistry station. Input/output lane 276 can be served by a sample handler station 280 that uses subpaths 277 and 278 to buffer samples for insertion or removal of the samples from the main track 272.

In some embodiments, the sample handler 280 can also load and unload samples or other payloads to/from the carriers 250A and 250B. This allows the number of carriers to be reduced to the amount needed to support payloads that are currently being used by the stations in track system 270, rather than having a vast majority of carriers sitting idle on tracks 277 and 278 during peak demand for the analyzer. Instead, sample trays (without the carriers disclosed herein) can be placed/removed by an operator at input/output lane 276. This can reduce the overall cost of the system and the number of carriers needed can be determined by the throughput of the analyzer, rather than based on anticipating the peak demand for the analyzer in excess of throughput.

Intelligent Carriers

Whereas some embodiments may utilize passive pucks or trays (e.g., the puck is a simple plastic or rubber brick that lacks active or autonomous systems, power, onboard processing, or control) to reduce cost and complexity, in some embodiments, the added complexity and cost necessary to integrate intelligence and autonomy into individual carriers (which can include intelligent pucks or trays in some embodiments) can provide certain benefits. Accordingly, some embodiments of the present invention can utilize intelligent independent carriers to enable certain improvements over passive pucks on friction-based tracks. For example, one disadvantage of prior art track systems is that, at each decision point, the decision for directing a puck is made by the track by rotating the puck and reading a barcode optically. Rotating and optical reading is a relatively slow process. Furthermore, this process can be redundant because the system has prior knowledge of the identification of the sample tube when the sample tube is placed into the puck by an operator. Some embodiments of the present invention can include carriers that have means to identify the contents of the sample tube (and optionally communicate this information to the automation system) without requiring the carrier to be stopped, rotated, and read optically.

For example, a carrier can include an onboard optical reader to automatically read a barcode of a payload. The results of the scan can then be stored in the memory of a carrier if the carrier has onboard processing capability. Alternatively, an outside source, such as a hand barcode reader operated by an operator at the time of placing the sample into the carrier, can communicate the barcode information of the payload to the carrier via RF signal or other known means, such as education protocol using temporary electrical contact or optical communication. In some embodiments, the association of the carrier with the payload can be stored external to the carrier and the identity of the carrier can be conveyed by the carrier to the system by RF, optical, or near-field communication, allowing the system to assist in routing or tracking the carrier and the payload. Routing decisions can then be made by the carrier or by identifying the carrier, rather than reading a unique barcode of a payload.

By moving processing capability and/or sensor capability onto each individual carrier, the carriers can participate actively and intelligently in their own routing through the track system. For example, if individual carriers can move independently of one another either by autonomous motive capabilities or by communication with the track, certain performance advantages can be realized.

By allowing carriers to move independently, carriers can move around the track faster. One limitation on the motion of a carrier is that it should not spill an open-tube sample. The limiting factor is generally not the velocity of the carrier in a straight line, but the acceleration and jerk experienced by the carrier (while speeding up, slowing down, or turning), which may cause splashing. For prior-art friction-based track systems, the velocity of the track is typically limited to prevent acceleration and jerk experienced by pucks from exceeding threshold amounts because the entire track moves. However, by using a track system with independently operating sections that can respond to individual carriers, or individual carriers that have independent motive capability, the acceleration of any given carrier can be tailored to limit acceleration/deceleration and jerk, while allowing the average velocity to be greater than that of traditional tracks. By not limiting the top speed of a carrier, the carrier can continue to accelerate on each track section as appropriate, resulting in a substantially higher average speed around the track. This can assist the carrier in traversing the entire track system in less than one machine cycle of the analyzer. These machine cycles can be, for instance, 20 or 40 seconds.

Similarly, an intelligent carrier can know its own identity and that of its payload. This allows the carrier to actively participate or assist in the routing decision process at individual decision points. For example, upon reaching a decision point (e.g., switch, intersection, junction, fork, etc.), a carrier can communicate its identity and/or the identity of its payload to the track or any switching mechanism (or its intended route that the carrier has determined based on the payload identity), via RF or near-field communication. In this scenario, the carrier does not need to be stopped at a decision point for a barcode scan. Instead, the carrier can keep going, possibly without even slowing down, and the carrier can be routed in real time. Furthermore, if the carrier knows where it is going or communicates its identity to the track (such that the track knows where the carrier is going) before the carrier physically reaches a decision point, the carrier can be made to decelerate prior to a decision point if the carrier will be turning. On the other hand, if the carrier does not need to turn at the decision point, the carrier can continue at a higher velocity because the sample carried by the carrier will not undergo cornering forces if the carrier is not turning at the decision point or a curved section of the track.

An intelligent carrier can also include onboard processing and sensor capabilities. This can allow a carrier to determine where it is on the track and where it needs to go, rather than being directed by the track (although, in some embodiments, a central controller sends routing instructions to the carrier to be carried out). For example, position encoding or markers in the track can be read by a carrier to determine the carrier's location. Absolute position information can be encoded on a track surface to provide reference points to a carrier as it traverses the track. This position encoding can take many forms. The track may be encoded with optical markers that indicate the current section of the track (e.g., like virtual highway signs), or may further include optical encoding of the specific absolute location within that section of track (e.g., like virtual mile markers). Position information can also be encoded with markings between absolute position marks. These can provide synchronization information to assist a carrier in reckoning its current trajectory. The optical encoding scheme may take on any appropriate form known to one skilled in the art. These marks used by the encoding scheme may include binary position encoding, like that found in a rotary encoder, optical landmarks, such as LEDs placed in the track at certain positions, barcodes, QR codes, data matrices, reflective landmarks, or the like. General position information can also be conveyed to the carrier via RF/wireless means. For example, RFID markers in the track can provide near field communication to the carrier to alert the carrier that it has entered a given part of the track. In some embodiments, local transmitters around or near the track can provide GPS-like positioning information to enable the carrier to determine its location. Alternatively, sensors in the track, such as Hall effect sensors or cameras, can determine the position of individual carriers and relay this information to the carrier.

Similarly, the carrier can have sensors that indicate relative motion, which provide data that can be accumulated to determine a position. For example, the carrier may have gyroscopes, accelerometers, or optical sensors that observe speckle patterns as the carrier moves to determine velocity or acceleration, which can be used to extrapolate a relative position.

Because a carrier can know where it is and its motion relative to the track, a carrier can essentially drive itself, provided it knows its destination. The routing of the carrier can be provided in many different ways in various embodiments. In some embodiments, when a carrier is loaded with the sample, the system can tell the carrier the destination analyzer station. This information can be as simple as the identification of the destination station in embodiments where the carrier has autonomous routing capability. This information can also be detailed information such as a routing list that identifies the specific path of the individual track sections and decision points that a carrier will traverse. Routing information can be conveyed to the carrier via any communication method described herein, such as RF communication, nearfield/inductive communication, electrical contact communication, or optical communication.

In an exemplary embodiment, when an operator scans the barcode of the sample tube and places it in a carrier, the system determines the identity of the carrier and matches it with the identity of the sample. The system then locates the record for the sample to determine which tests the sample must undergo in the analyzer. A scheduler then allocates testing resources to the sample, including choosing which tests will be done by individual testing stations and when the sample should arrive at each testing station for analysis. The system can then communicate this schedule (or part of the schedule) to the carrier to inform the carrier of where it needs to go, and optionally when it needs to go and/or when it needs to arrive.

Once the carrier is placed onto the track system, the routing capabilities and location acquisition systems of the carrier enable the carrier to determine where it is on the track and where it needs to go on the track. As the carrier traverses the track, the carrier reaches individual decision points and can be directed along the main track or along subpaths, as appropriate. Because each carrier operates independently from one another, a carrier can do this quite quickly without necessarily stopping at each decision point and without waiting for other carriers in a queue. Because these carriers move quickly, there is less traffic on the main sections of the track, which reduces the risk of collision or traffic jams at decision points or corners in the track (e.g., sections where carriers might slow down to avoid excessive forces on the sample).

Motive force can be provided to the carriers in many ways. In some embodiments, the track actively participates in providing individualized motive force to each carrier. In some embodiments, motive force is provided by electromagnetic coils in the track that propel one or more magnets in the carrier. An exemplary system for providing this motive force is the track system provided by MagneMotion, Inc., which can generally be understood by the description of the linear synchronous motors (LSMs) found in US Published Patent Application 2010/0236445, assigned to MagneMotion, Inc. These traditional systems utilizing this magnetic motion system have included passive carriers that lack the integrated intelligence of the carriers described herein, and all routing and decisions are made by a central controller with no need for active carriers that participate in the routing and identification process.

In embodiments that utilize magnetic motion, the electromagnetic coils and the magnets operate as an LSM to propel each individual carrier in the direction chosen with precise control of velocity, acceleration, and jerk. Where each coil on the track (or a local set of coils) can be operated independently, this allows highly localized motive force to individual carriers such that individual carriers can move with their own individually tailored accelerations and velocities. Coils local to a carrier at any given moment can be activated to provide precise control of the direction, velocity, acceleration, and jerk of an individual carrier that passes in the vicinity of the coils.

In some embodiments, a track may be comprised of many individually articulable rollers that act as a locally customizable friction track. Because individual micro-sections of the track can be managed independently, rollers immediately around a carrier may be controlled to provide individualized velocity, acceleration, and jerk. In some embodiments, other active track configurations can be used that provide localized individual motive force to each carrier.

In some embodiments, the track may be largely passive, providing a floor, walls, rails, or any other appropriate limitations on the motion of a carrier to guide the carrier along a single dimension. In these embodiments, the motive force is provided by the carrier itself. In some embodiments, each individual carrier has one or more onboard motors that drive wheels to provide self-propelled friction-based motive force between the track and the carrier. Unlike traditional friction tracks, where the track is a conveyor, carriers with driven wheels can traverse the track independently and accelerate/decelerate individually. This allows each carrier to control its velocity, acceleration, and jerk at any given moment to control the forces exerted on its payload, as well as traverse the track along individually tailored routes. In some embodiments, permanent magnets may be provided in the track and electromagnets in the carrier may be operated to propel the carrier forward, thereby acting as an LSM with the carrier providing the driving magnetic force. Other passive track configurations are also contemplated, such as a fluid track that allows carriers to float and move autonomously via water jets or the like, a low friction track that allows carriers to float on pockets of air provided by the track, (e.g., acting like a localized air hockey table), or any other configuration that allows individual carriers to experience individualized motive forces as they traverse the track.

Figure 5:
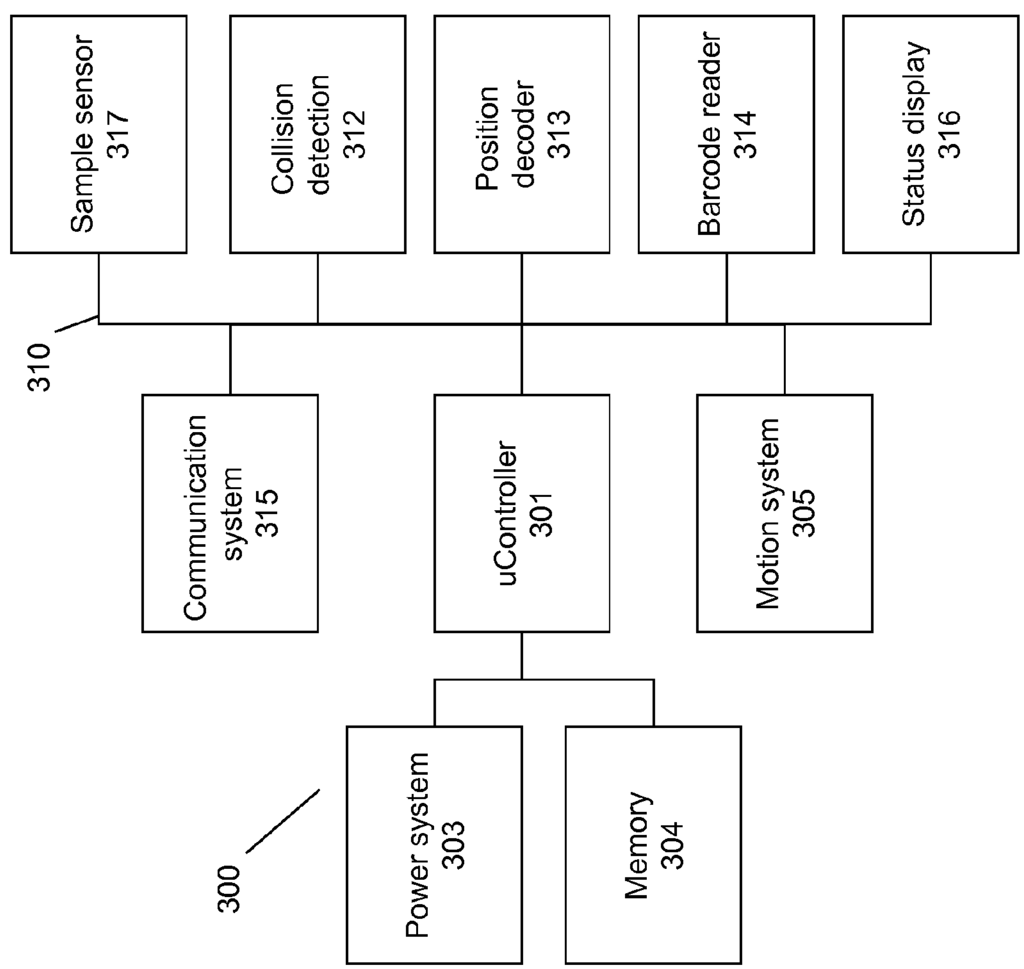
FIG. 5 is a system block diagram of the control systems including onboard active carriers that can be used with certain embodiments disclosed herein.

FIG. 5 shows a top level system diagram of the control systems and sensors for an exemplary intelligent autonomous carrier 300. Carrier 300 is controlled by a microcontroller 301 that includes sufficient processing power to handle navigation, maintenance, motion, and sensor activities needed to operate the carrier. Because the carrier is active and includes onboard electronics, unlike prior art passive carriers, the carrier includes an onboard power station. The details of this station vary in different embodiments of the present invention. In some embodiments, power system 303 comprises a battery that may be charged as the carrier operates while, in other embodiments, the battery is replaceable or can be manually charged when the carrier is not operating. Power system 303 can include the necessary charging electronics to maintain a battery. In other embodiments, the power system 303 comprises a capacitor that may be charged by inductive or electrical contact mechanisms to obtain electrical potential from the track itself, in much the same way a subway car or model train might receive power.

Microcontroller 301 communicates with system memory 304. System memory 304 may include data and instruction memory. Instruction memory in memory 304 includes sufficient programs, applications, or instructions to operate the carrier. This may include navigation procedures as well as sensor handling applications. Data memory in memory 304 can include data about the current position, speed, acceleration, payload contents, navigational plan, identity of the carrier or payload, or other status information. By including onboard memory in carrier 300, the carrier can keep track of its current status and uses information to intelligently route around the track or convey status information to the track or other carriers.

Microcontroller 301 is responsible for operating the motion system 305, sensors 312, 313, and 314, and communication system 315, status display 316, and sample sensor 317. These peripherals can be operated by the microcontroller 301 via a bus 310. Bus 310 can be any standard bus, such as a CAN bus, that is capable of communicating with the plurality of peripherals, or can include individual signal paths to individual peripherals. Peripherals can utilize their own power sources or the common power system 303.

Motion system 305 can include the control logic necessary for operating any of the motion systems described herein. For example, motion system 305 can include motor controllers in embodiments that use driven wheels. In other embodiments, motion system 305 can include the necessary logic to communicate with any active track systems necessary to provide a motive force to the carrier 300. In these embodiments, motion system 305 may be a software component executed by microcontroller 301 and utilizing communication system 315 to communicate with the track. Devices such as motors, actuators, electromagnets, and the like, that are controlled by motion system 305 can be powered by power system 303 in embodiments where these devices are onboard the carrier. External power sources can also provide power in some embodiments, such as embodiments where an LSM provides motive force by energizing coils in the track. In some embodiments, motion system 305 controls devices on or off the carrier to provide motive force. In some embodiments, the motion system 305 works with other controllers, such as controllers in the track, to coordinate motive forces, such as by requesting nearby coils in the track be energized or requesting the movement of local rollers. In these embodiments, motion system 315 can work together with communication system 305 to move the carrier.

Carrier 300 can include one or more sensors. In some embodiments, carrier 300 includes a collision detection system 312. Collision detection system 312 can include sensors at the front or back of a carrier for determining if it is getting close to another carrier. Exemplary collision detection sensors can include IR range-finding, magnetic sensors, microwave sensors, or optical detectors. Whereas many prior art pucks are round, carrier 300 may be directional, having a front portion and a rear portion. By having a directional geometry, carrier 300 can include a front collision detector and a rear collision detector.

In some embodiments, collision detection information can include information received via the communication system 315. For example, in some embodiments, the central controller for the track can observe the location and speed of carriers on the track and evaluate collision conditions and send updated directions to a carrier to prevent a collision. In some embodiments, nearby carriers can communicate their positions in a peer-to-peer manner. This allows carriers to individually assess the risk of collision based on real-time position information received from other carriers. It will be understood that in embodiments where the carrier receives trajectory information about other carriers, or decisions are made with the help of a centralized controller that has access to trajectory information of nearby carriers, the carriers need not be directional, and can include sensors or receivers that do not depend on a given orientation of a carrier.

Carrier 300 can also include a position decoder 313. This sensor can extrapolate the carrier's position as described herein. For example, position decoder 313 can include a camera or other optical means to identify landmarks in the track or observe optical encoding in the track. In some embodiments, position decoder 313 can also include inertial sensors, magnetic sensors, or other sensors sufficient to determine a carrier's current position, direction, velocity, acceleration, and/or jerk. In some embodiments, the components of the position decoder 313 can operate as part of the communication system. For example, in some embodiments, optical markings in the track can be electronically rewriteable, such as via an LCD or E-ink display, and can be used by a central controller to convey routing instructions, along with position information. In these embodiments, image sensors used to determine position can also be used to receive the routing instructions or other data being communicated to the carrier.

Carrier 300 can optionally include a barcode reader 314. If equipped with the barcode reader 314, carrier 300 can observe the barcode of its payload at the time the samples are loaded onto the carrier or at any time thereafter. This prevents the need for a carrier to stop at individual decision points to have the system read the barcode of a sample tube. By reading and storing the identity of the sample tube, or conveying this information to the overall system, a carrier may more efficiently traverse the track system because routing decisions can be made in advance of reaching a decision point. Alternatively, where a system knows the identity of the sample when it is placed onto the carrier, the system can include an external barcode reader and can convey the identity of the payload to the carrier for storage and memory 304 via communication system 315.

Communication system 315 can comprise any mechanisms sufficient to allow the carrier to communicate with the overall automation system. For example, this can include an XBee communication system for wireless communication using an off-the-shelf communication protocol, such as 802.15.4, any appropriate version of 802.11, or any standard or proprietary wireless protocol. Communication system 315 can include a transceiver, antenna, and logic for operating an RF communication protocol. In some embodiments, communication system 315 can also include near-field communication, optical communication, or electrical contact components. Information conveyed via the communications system to/from carrier 300 is described throughout this application.

In some embodiments, the carrier can also include a status display module 316. The status display module 316 can include a controller and rewritable electronic display, such as an LCD panel or E-ink display. In some embodiments, the controller is treated as an addressable portion of memory, such that the microcontroller 301 can easily update the status display 316.

In some embodiments, the carrier also includes sample sensor 317. This sensor can be used to indicate the presence or absence of a fluid container in the carrier's tube bracket (which may also be referred to as a tube holder). In some embodiments, this is a momentary mechanical switch that is depressed by the presence of a tube and not depressed when a tube is absent. This information can be used to determine the status of a tube, which can assist in the display status information by status display module 316.

Routing and Positioning

The desire for rapid transit times within an analyzer system can make routing difficult. In prior art systems, rapid routing is less critical because samples are generally stopped, singulated, and scanned at each decision point. In those systems, the routing decision for a given decision point can be made while the sample is stopped. Rapid routing decisions are generally desired, and may require determining a switching decision before a sample carrier reaches a decision point. Furthermore, because the carriers move at a rapid rate compared to the prior art, the control of the instantaneous trajectory of a sample carrier can be assisted by real-time processing in order to prevent spilling or damaging IVD samples. In some embodiments, substantially instantaneous trajectory observation and control is conducted on-board each carrier to facilitate real-time control, while the overall routing decisions are made by a central controller that manages a group of carriers. Therefore, in some embodiments of the present invention, the carriers act like semi-autonomous robots that receive global routing instructions from a central controller, but make local motion decisions substantially autonomously.

Figure 6:
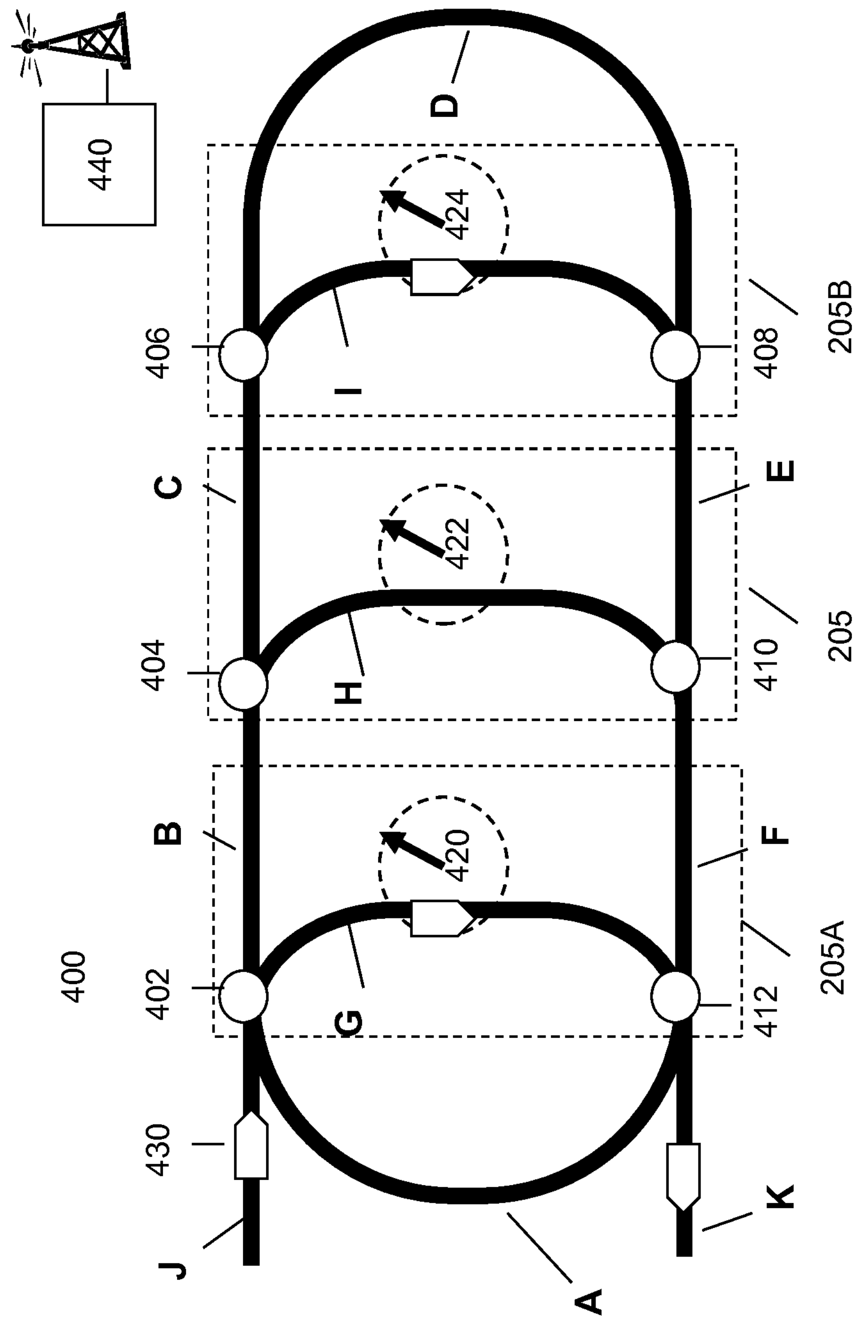
FIG. 6 is a diagrammatic view of exemplary routes in an exemplary track configuration that can be used for navigation of sample carriers in certain embodiments.

The exemplary track 400 shown in FIG. 6 includes a first curve segment A that connects to straight segment B and a pullout segment G, (e.g., a segment that serves a testing station), which serves analyzer testing station 205A and pipette 420, via decision point 402. Segment B connects to straight segment C and a pullout segment H, which serves analyzer/testing station 205 and pipette 422, via decision point 404. Segment C connects to curved segment D, which serves sample handling station 205C and a pullout segment I, which serves analyzer/testing station 205B and pipette 424, via decision point 406. Segment D connects to straight segment E and the other end of pullout segment I, via decision point 408. That is, there are different paths between decision points 406 and 408—segments D and I (where segment I is a pullout that can be used to deliver samples to interact with pipette 424). Segment E connects to straight segment F and the other end of pullout segment H, via decision point 410. Segment F connects to curved segment A and the other end of pullout segment G, via decision point 412. In some embodiments, track 400 includes input and output lanes J and K, which can be used to add or remove carriers at decision points 402 and 412. Central management processor 440 uses the status information of the carriers and track as well as the identity of samples or other payload carried by the carriers and the required assays to be performed by the system on these samples.

In some embodiments, decision points 402-412 are passive forks in the track that carrier 430 can navigate to select a proper destination segment. In other embodiments, decision points 402-412 are active forks that can be controlled by carrier 430 or central management processor 440. In some embodiments, decision points 402-412 are electromagnetically controlled switches that respond to requests by carrier 430, such as via RF or near field communication. In some embodiments, these electromagnetically controlled switches have a default position, such as straight, which the switch will return to once a carrier has been routed. By using default positions for decision points, a carrier may not need to request a position at each decision point, unless it needs to be switched at that decision point.

In an exemplary schedule, central management processor 440 assigns carrier 430 to a first route to place the carrier 430 and its payload within reach of pipette 420. Carrier 430 is instructed to travel along segment J to decision point 402 and travel onto segment G to stop at a position accessible to pipette 420. In some embodiments, carrier 430 receives the instructions and determines its current location and trajectory to determine a direction and trajectory to use to reach decision point 402. Carrier 430 can also take into account that it will be making a hard right turn at decision point 402 onto segment G. In some embodiments, decision point 402 includes a switching mechanism in the track that can operate under the control of carrier 430. In these embodiments, carrier 430 communicates with the track on approach to decision point 402 to request switching onto segment G. In other embodiments, carrier 430 may have a steering mechanism (such as moveable guide wheel, directional magnets, asymmetric brakes, or the like) that allows carrier 430 to make a right turn onto segment G at decision point 402, without the assistance of an external gate integrated into the track. In these embodiments, carrier 430 engages the steering mechanism at decision point 402 to make the turn onto segment G.

Carrier 430 can determine its rough location—its current track section, such as section J, by reading encoding in the track, such as optical encoding, or RFID tags. In some embodiments, carrier 430 uses multiple means to determine its location within the track system 400. For example, RFID tags can be used to determine generally on which track segment the carrier 430 is located, while optical encoding or other precise encoding can be used to determine the position within that track segment. This encoding can also be used to determine velocity, acceleration, or jerk by observing changes in the encoding (e.g., derivatives from the position information).

Carrier 430 can use the identification of the current track section to determine the appropriate route to the destination section either by explicit instruction received by the central management processor 440 or by looking up an appropriate route in an onboard database in memory 304, as shown in the onboard control systems in FIG. 5. In some embodiments, the carrier 430 has an understanding of how to reach section G from section J based on a map stored in the memory of carrier 430 in memory 304. This map can include a simple lookup table or a tree of track sections where each node is linked by the corresponding decision points, or vice versa. For example, upon identifying that the carrier is currently in the track section J, the onboard database can inform carrier 430 to proceed to decision point 402 to be switched to the right onto section G.

Linear Random Access Queues

Routing and sample handling within an analyzer can benefit from linear queues placed at certain locations within the automation system. These linear queues can provide both FIFO and random-access capabilities without greatly increasing the amount of space needed.

Figure 7:
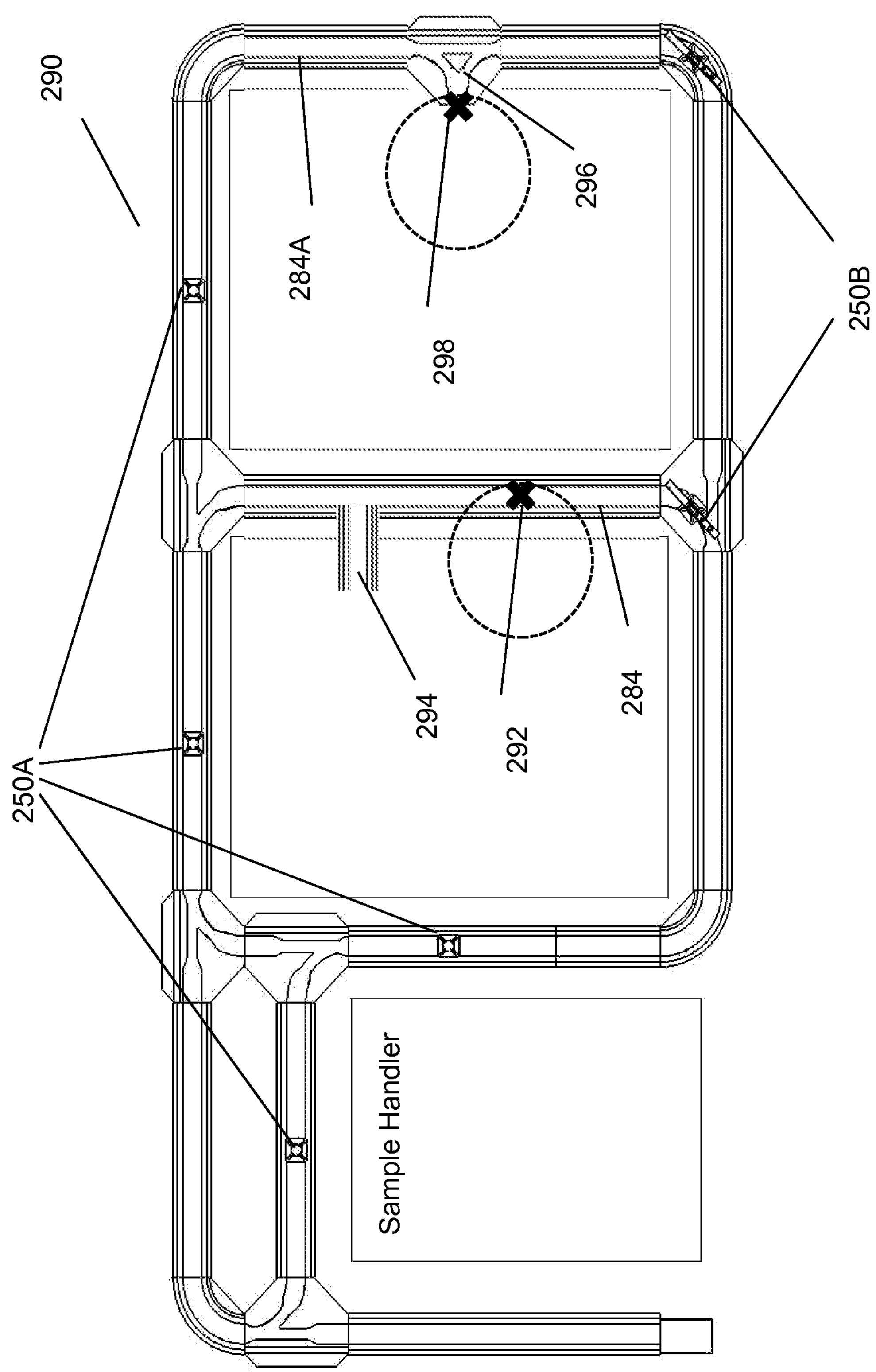
FIG. 7 is a top view of an exemplary automation systems carrier that can be used with the embodiments disclosed herein.

FIG. 7 shows an exemplary automation system 290, which employs linear random-access on track sections 284 and 284A. Like automation system 270, automation system 290 employs track sections that act as a main track with sub-paths, such as track sections 284, and 284A. Track sections 284 and 204A act as sidecars to provide local access to modules within the analyzer. These track sections provide transportation to carriers 250A to reach modules within the system. Because these track sections provide access to the modules, they have a predetermined length. The length of these track sections can make them suitable for physical buffering of multiple carriers should the module being served by the track section require a buffer or queue. Ordinarily, buffering on a track section provides a FIFO queue with all of the inherent limitations of FIFO queue. However, embodiments of the present invention can utilize storage locations accessible to use track sections to enable carriers to be reordered within the track section. This can provide the benefits of random-access queues, while still utilizing the track section itself for the space used by the queue.

Automation system 290 includes two illustrative storage locations. Track section 284 provides access to a local module via location 292. Location 292 is accessible to a pipette on the module. By placing a sample carrier at location 292, a volume of a sample being carried can be aspirated. The local track section 284 can provide a physical queue for sample carriers to reach location 292. Storage location 294 can be employed to temporarily remove sample carriers from the main portion of track section 284. By moving a portion of the queue to allow a single sample or multiple samples to be stored in storage location 294, an arbitrary sample can be selected from within the otherwise linear queue. This can provide random-access to at least a portion of the samples. Once a sample is stored in storage location 294, one or more carriers within the queue can then be moved with respect to storage location 294, such that the sample stored in location 294 can be reintroduced to the queue on track section 284 at a different position within the queue than the position from which the sample was originally removed. In this manner, storage location 294 can be used to reorder samples within the linear queue on track section 284. By selectively reordering the otherwise FIFO queue, random access to samples can be provided.

Track section 284A illustrates an alternative storage location approach to provide random-access to samples within a physical queue. In this example, location 298 is accessible to a pipette of the local module. By moving a sample to position 298, a volume of sample can be aspirated. Location 298 is not on the main portion of track section 284A. Rather, location 298 is within the storage location 296. Samples in the queue on the track section 284A can move forward and backwards to allow random access to samples within the queue to be shifted into storage location 296 to provide access to the sample at location 298 within the storage rotation.

The exemplary implementations of storage locations on track sections 284 and 284A can provide both FIFO and random access to samples for use by the local modules. Furthermore, because the storage location approach allows the local module to control and reorder samples in local queues, the approach can work with many different types of tracks. For example, track section 284 can be a friction track, a magnetic track, a passive track, or any other track suitable for allowing samples on carriers to be moved forward and backwards within the queue. Some embodiments of the present invention utilize a track section for the queue that provides bidirectional functionality to allow samples to move forward or backwards within the track section. Furthermore, the type of carrier and payload can be any suitable carrier and payload described herein. For example suitable carriers can include carriers 250A, which carry individual samples. Suitable carriers may also include carriers 250B, which can carry reagents as the payload. The queues within the local track sections can include both samples and reagents, or any other payload. For example, a queue might include a mix of sample carriers and reagent carriers. This can allow a pipette to access a reagent and the corresponding sample when performing a single assay. By providing random-access within the queue, the order in which samples or reagents arrive at the local track section need not match the order in which these samples or reagents will be used.

Figure 8:
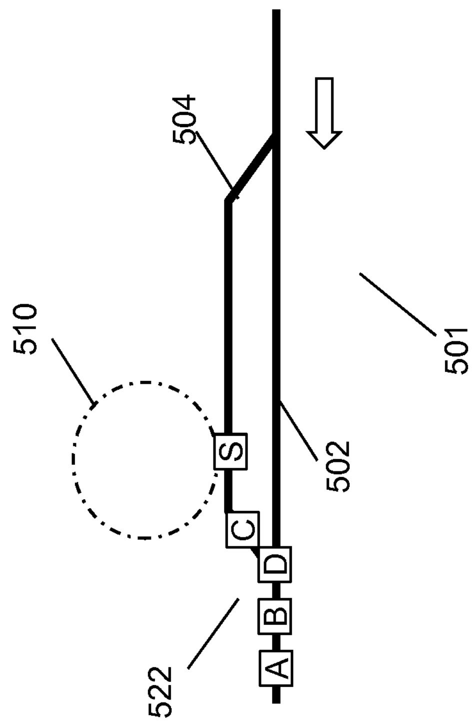
FIG. 8 is diagrammatic view of a FIFO queue in a sidecar similar to the prior art.
Figure 8:
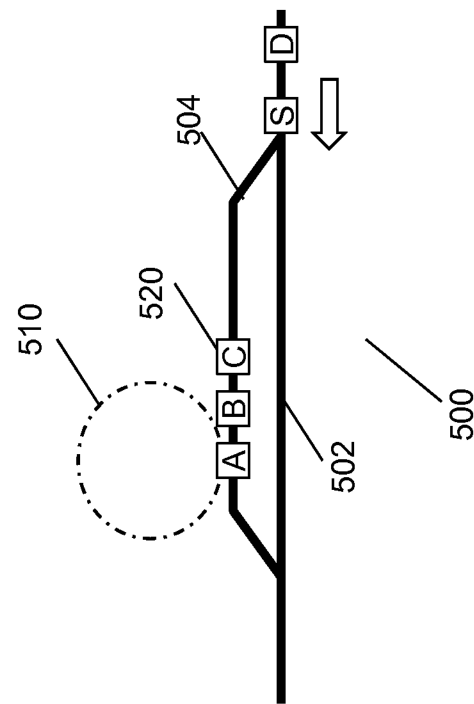

FIG. 8 illustrates an exemplary FIFO queue in a prior art sidecar. Samples can traverse a main track 502, or be directed to a sidecar 504 for interaction with a local testing module. Pipette 510 is provided to allow access to samples on the sidecar. In a first condition 500, a local queue 520 comprises samples A, B, and C. Queue 520 is a FIFO queue. Sample A will be aspirated, followed by sample B, followed by sample C. This situation may be suitable, so long as all samples are of the same priority and the local module is prepared for each sample in succession.

This approach can be problematic, however, when a STAT sample arrives. As shown in condition 501, when a STAT sample is directed onto sidecar 504, it takes priority. Because random-access is not provided, queue 520 must be flushed onto the main track. In this example, sample D was already on the main track when queue 520 was dumped onto the main track 502. As can be seen, group 522 now has sample D between samples B and C. Thus, once samples A, B, and C loop back around the track to once again be on sidecar 504, they may be out of the original order if sample D is also directed onto sidecar 504. Furthermore, it may take several sample cycles of the local analyzer module before samples A, B, and C return to sidecar 504. This can result in wasted downtime of the local analyzer module. Furthermore, if specific reagents were being prepared for sample A, those reagents may be wasted if the resource preparing the reagents is used by other samples before sample A can return to sidecar 504.

Figure 9:
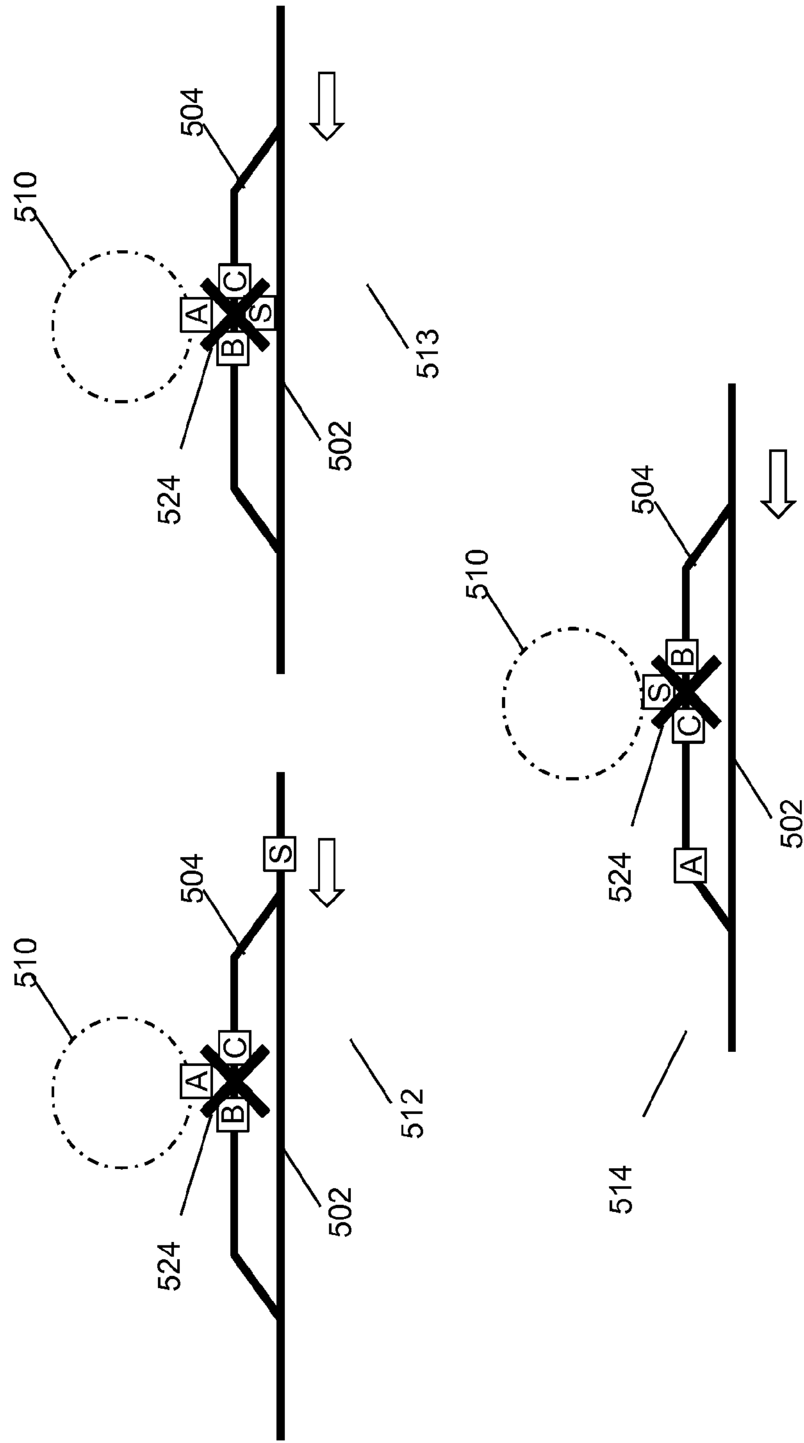
FIG. 9 is diagrammatic view of a carousel queue in a sidecar similar to the prior art.

FIG. 9 demonstrates a prior art approach to a random access queue provided by a carousel 524. In this example, the carousel is small, but the carousel will grow quickly in area as the number of positions in the carousel increases. This can limit the amount of available positions within a carousel, and limit the size of the queue on sidecar 504. In condition 512, samples A, B, and C were directed onto sidecar 504 off main track 502 and placed into carousel 524. Sample A interacts with pipette 510. In condition 513, when a STAT sample arrives onto sidecar 504, it can be placed into a position in carousel 524, while sample A finishes interacting with pipette 510. Once pipette 510 finishes aspirating from sample A, at condition 514, sample A can be released from the carousel via sidecar 504 to main track 502. Because carousel 524 provides a random access to samples held in the carousel, samples A, B, and C can remain in the carousel, while the carousel rotates to allow the STAT sample to interact with pipette 510. Carousel 524 can add complexity, cost, and take up valuable real estate within the analyzer.

Figure 10B:
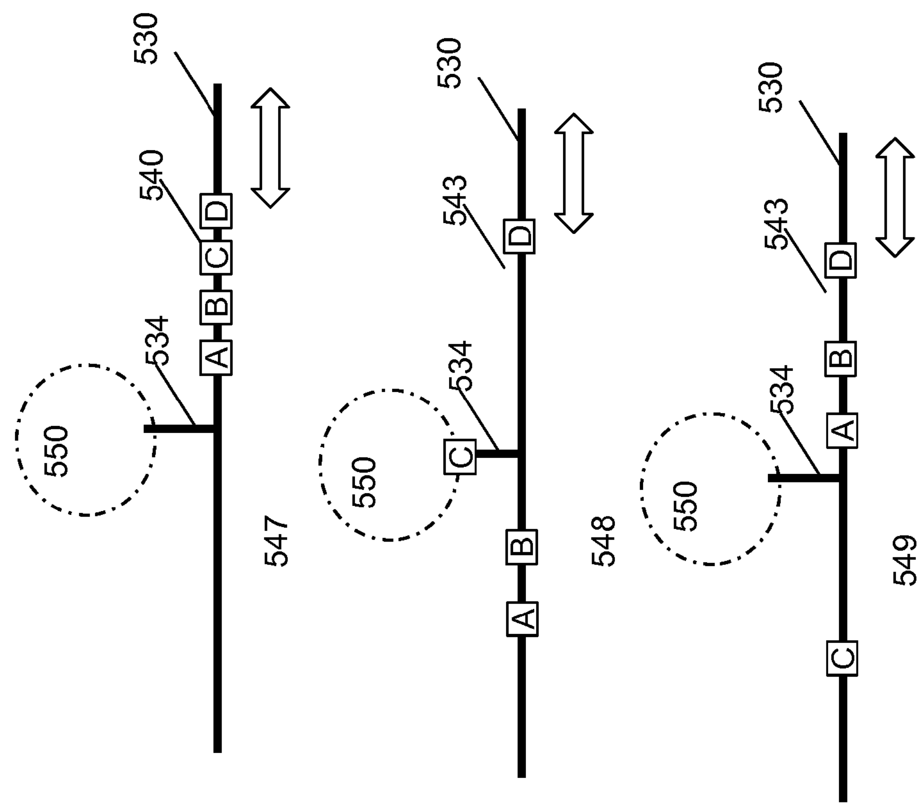
FIGS. 10A-B are diagrammatic views of linear track configurations that can be used for random access and FIFO queuing in exemplary embodiments of the present invention.
Figure 10A:
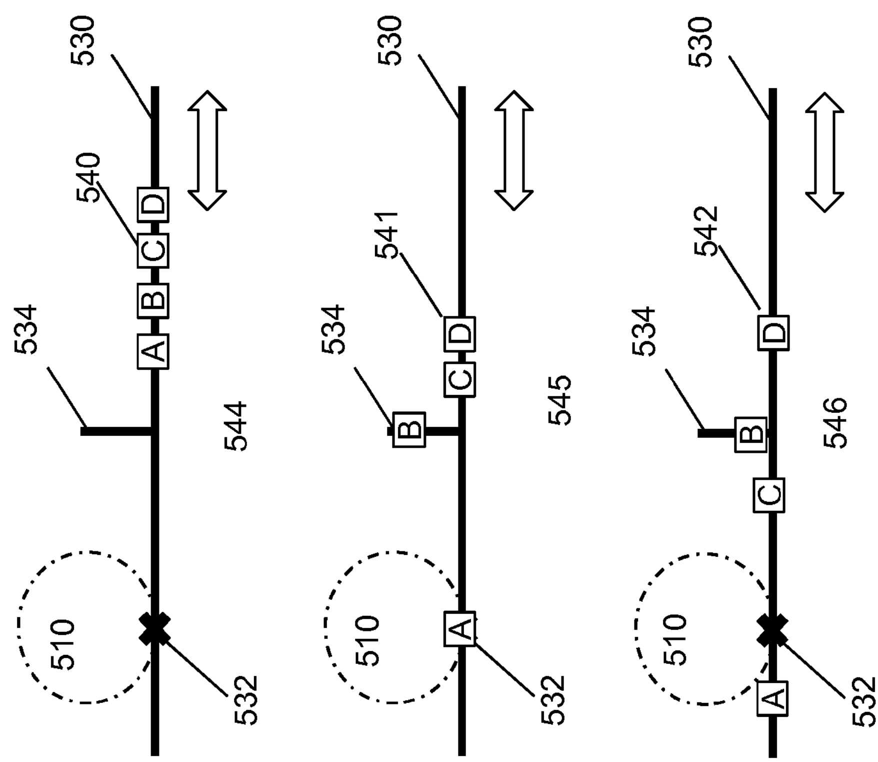

FIG. 10A shows an operational example of an embodiment of the present invention utilizing a storage location 534 that is accessible to track 530 to provide random access to samples within an otherwise FIFO queue 540. Here, pipette 510 can access track 530 at location 532. In condition 544, queue 540 is in the order of arrival: A, B, C, D. Samples arrive from the right and leave from left. At condition 545, sample A is moved to location 532 to allow pipette 510 to aspirate a volume of sample A. Meanwhile, a controller that handles the queue decides it prefers to access sample C before accessing sample B. Therefore, sample B is directed into location 534 for storage. This leaves a group 541, consisting of samples C and D. In condition 546, sample C is directed past storage location 534 so that pipette 510 can access sample C after it finishes with sample A. Meanwhile, sample B is directed out of storage location 534 back onto track 530 between samples C and D. This leaves sample D as the sole sample to the right of storage location 534.

FIG. 10B shows a similar operational example of another embodiment of a linear random-access queue utilizing a storage position. In this example, rather than providing access to a pipette at a location on track 530, pipette 550 can access samples in storage location 534. In condition 547, a queue 540 comprising samples A, B, C, and D arrives on track 530. In this example, the local module desires access to sample C before all other samples. In condition 548 samples A and B advance past storage location 534 on track 530, allowing sample C to be directed into storage location 534 for access by pipette 550. Once pipette 550 finishes aspirating from sample C at condition 549, samples A and B can be moved to the right of storage location 534, allowing sample C to egress to the left. In both conditions 548 and 549, the local queue 543 includes samples A, B, and D, while sample C can either be considered at the head of the queue or already selected and logically removed from the queue.

A STAT sample can be treated like sample C. That is, the local analyzer module can determine that sample C is a higher priority sample and access sample C out of order to comply with the STAT priority of the sample. Similarly, sample C may simply be a sample for which the local analyzer module determines it should access first, for efficiency or other reasons that will be apparent.

Figure 11A:
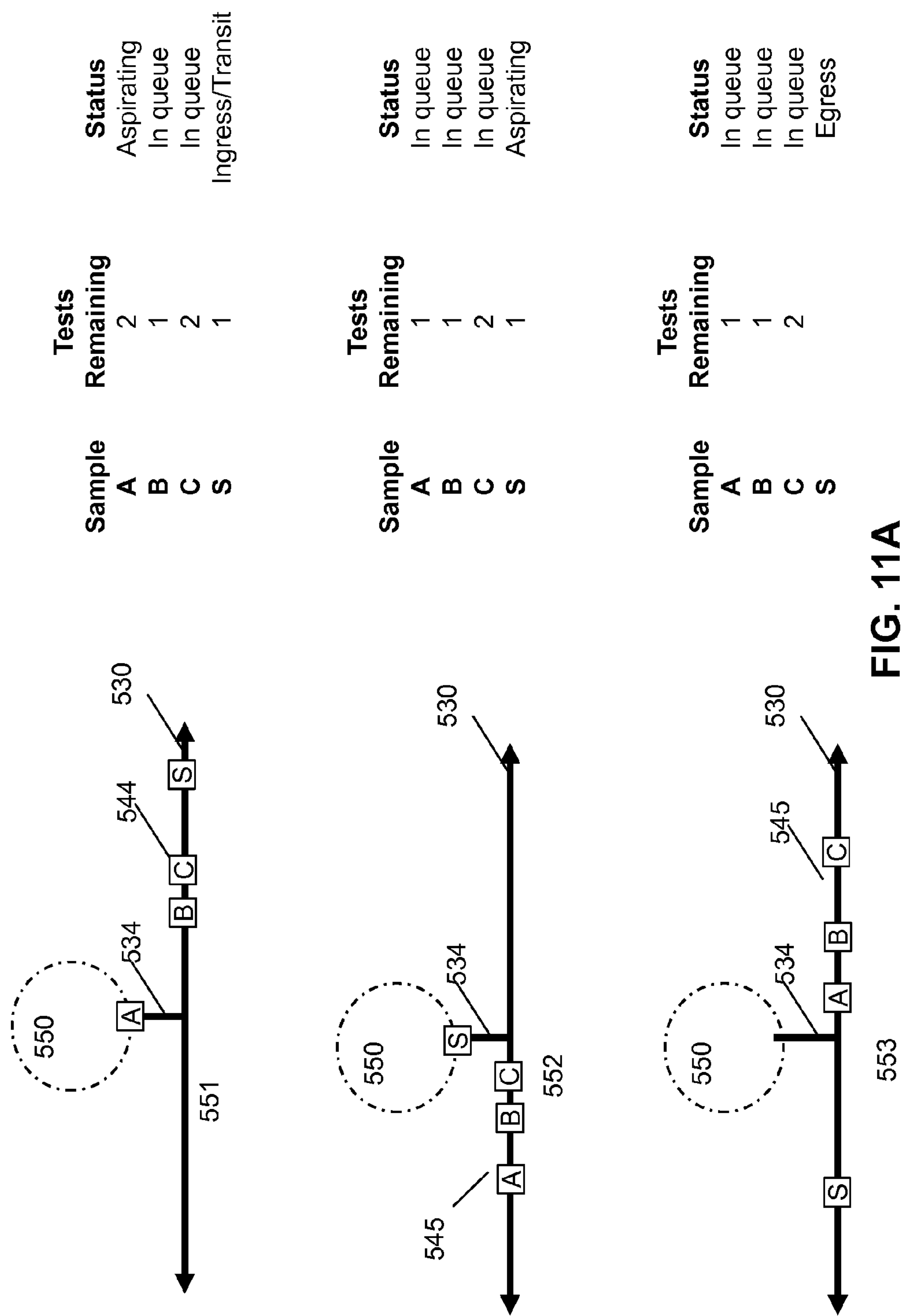
FIGS. 11A-C are is diagrammatic views of a linear track configuration and states that may be encountered during operation of random access and FIFO queuing in exemplary embodiments of the present invention.
Figure 11B:
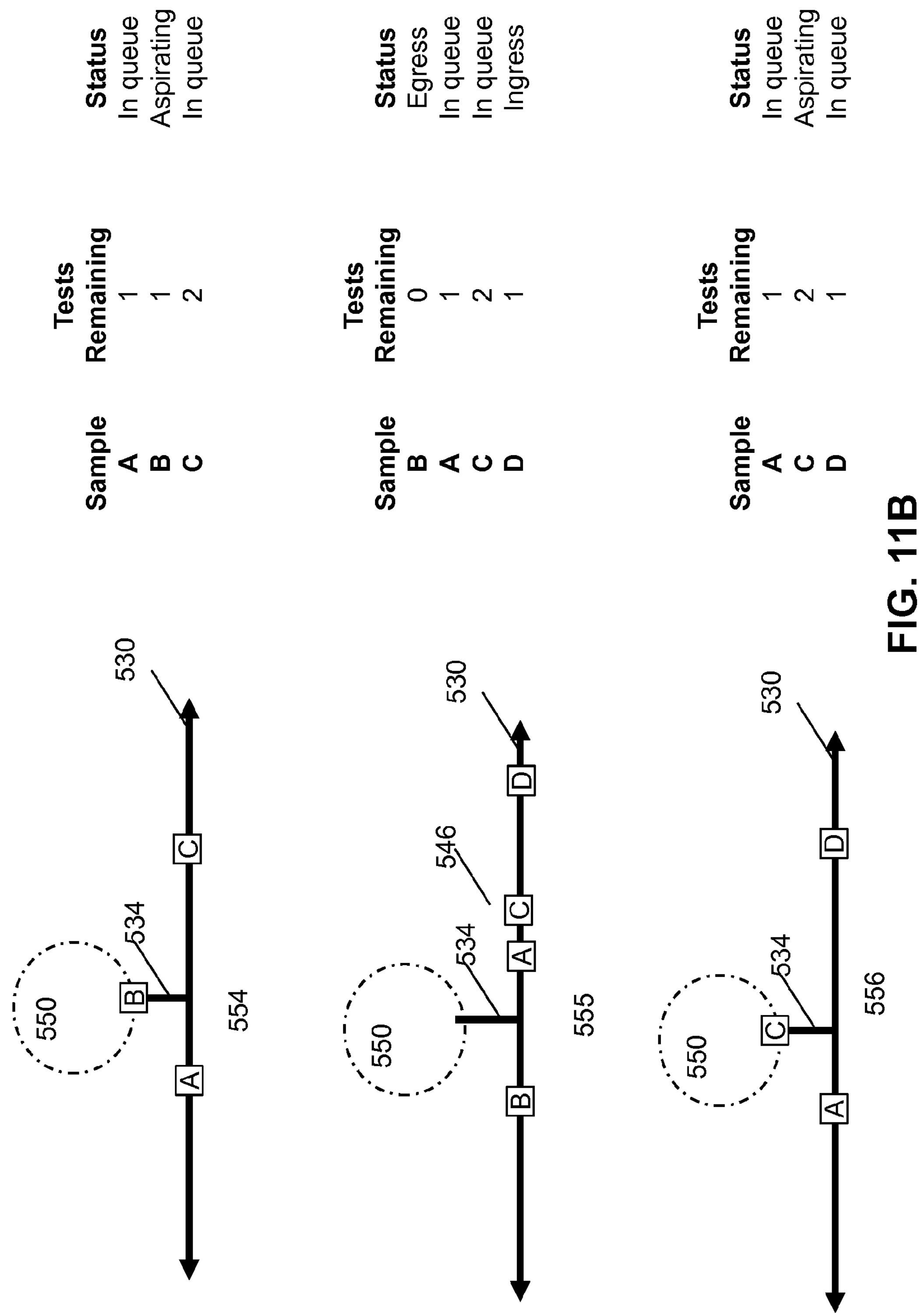
Figure 11C:
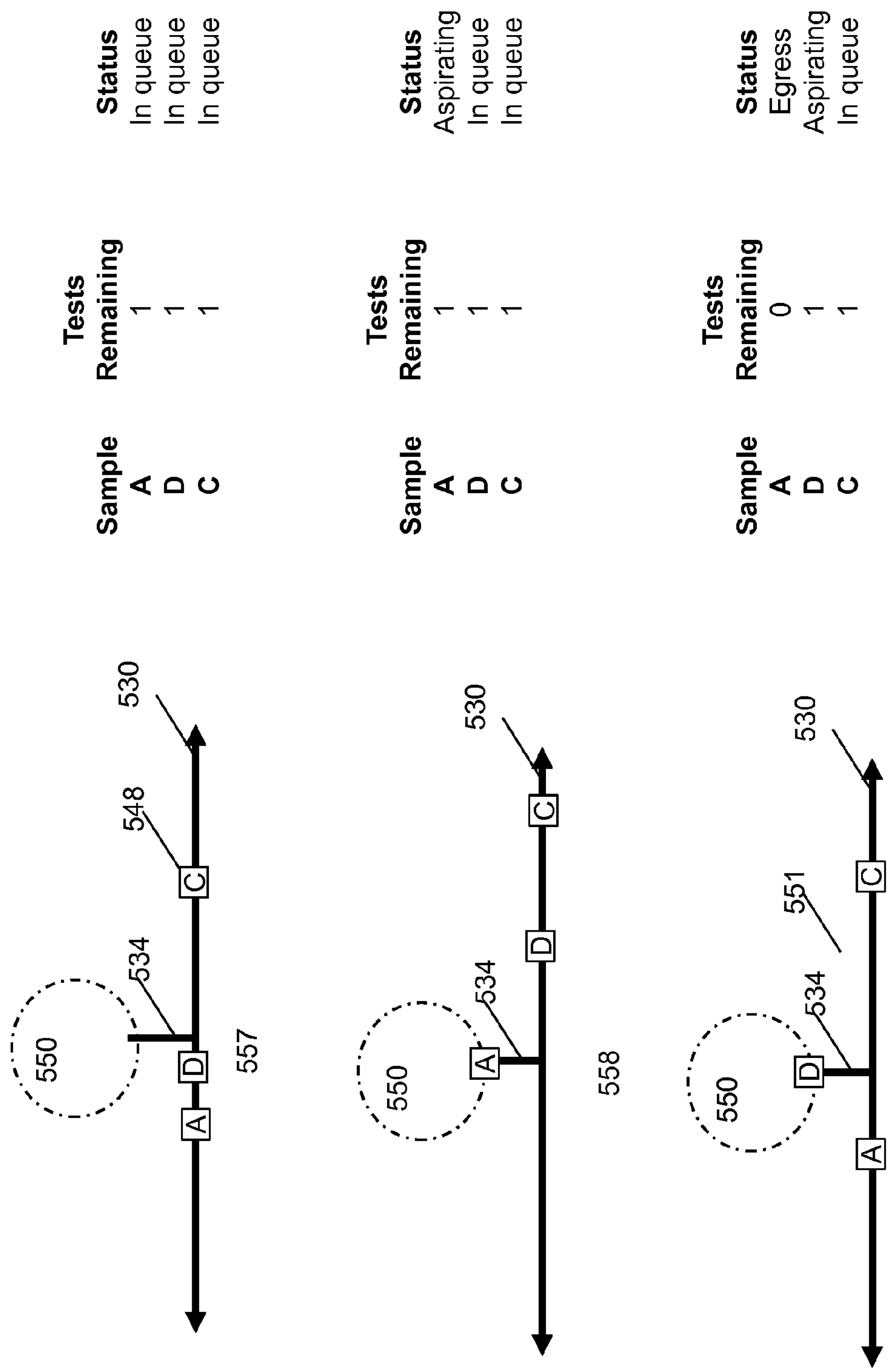

FIGS. 11A, B, and C illustrate a more complex operational situation. On the right side of these figures, a chart shows the number of tests remaining for each sample and the current status of the sample. On the left side, the location of each sample is shown. Samples enter to the right and leave to the left. In condition 551, sample A requires two tests. Here, each test requires a separate aspiration via pipette 550, which accesses samples via storage location 534 off of track 530. During normal operation, multiple tests may be performed on a sample in sequence, or the tests may be interleaved with tests on other samples. While sample A is aspirated, samples B and C form a queue 544 on track 530. Sample B has one test remaining, while sample C has two tests remaining. A STAT sample begins to arrive. At this point, the local analyzer module is either unaware of the STAT sample's impending arrival, or it has not yet logically added it to queue 544.

In condition 552, the local testing module notices the STAT sample and moves it into storage location 534 to allow testing to begin immediately. Meanwhile, sample A has been moved onto track 530 ahead of samples B and C. Samples A, B, and C form queue 545. Once the STAT sample is finished testing in condition 553, the STAT sample can be moved to the left side of track 530 to allow it to exit the local analyzer module. Meanwhile, queue 545 is moved to the right of storage location 534 to allow the egress of the STAT sample. In condition 554, a controller managing the queue of the local analyzer module determines that the next test should be performed on sample B. Sample A is moved to the left of storage location 534, while sample B is moved into storage location 534 for aspiration. This leaves sample C as the sole sample on track 530 to the right of storage location 534. At condition 555 sample B is moved out of the storage location and exits to the left of the storage location. Sample A is moved to the right of storage location 534 to allow sample B to exit. Meanwhile, a new sample arrives, sample D. This forms a new queue 546 comprising samples A, C, and D.

As shown in condition 556, the controller determines that sample C should be the next sample aspirated. Sample A is again moved to the left of storage location 534, allowing sample C to move into storage location 534 for aspiration. This leaves sampled D to the right of storage location 534. As shown in condition 557, the controller determines that the proper order for the queue 548 is A, D, C. Sample D is moved to the left of storage location 534, allowing sample C to be moved out of storage location 534 to be right of sample D. Note that the order of queue 548 is different from the queue 546 due to the reordering performed by storing samples in storage location 534 and shifting samples relative to storage position 534 while a sample is stored there.

As shown in condition 558, the local testing module utilizes the new order of the samples to access samples in a FIFO manner. Sample A is moved into storage location 534 for interaction with pipette 550. Next, in condition 559, sample A has completed all testing and is placed back onto track 530 to the left of sample D, to allow sample A to exit the track. Once sample A is on the track, sample D is moved into storage location 534 for aspiration. Sample C remains in the queue. Once the pipette 550 has finished aspirating from sample B, sample C can then be accessed.

Figure 12:
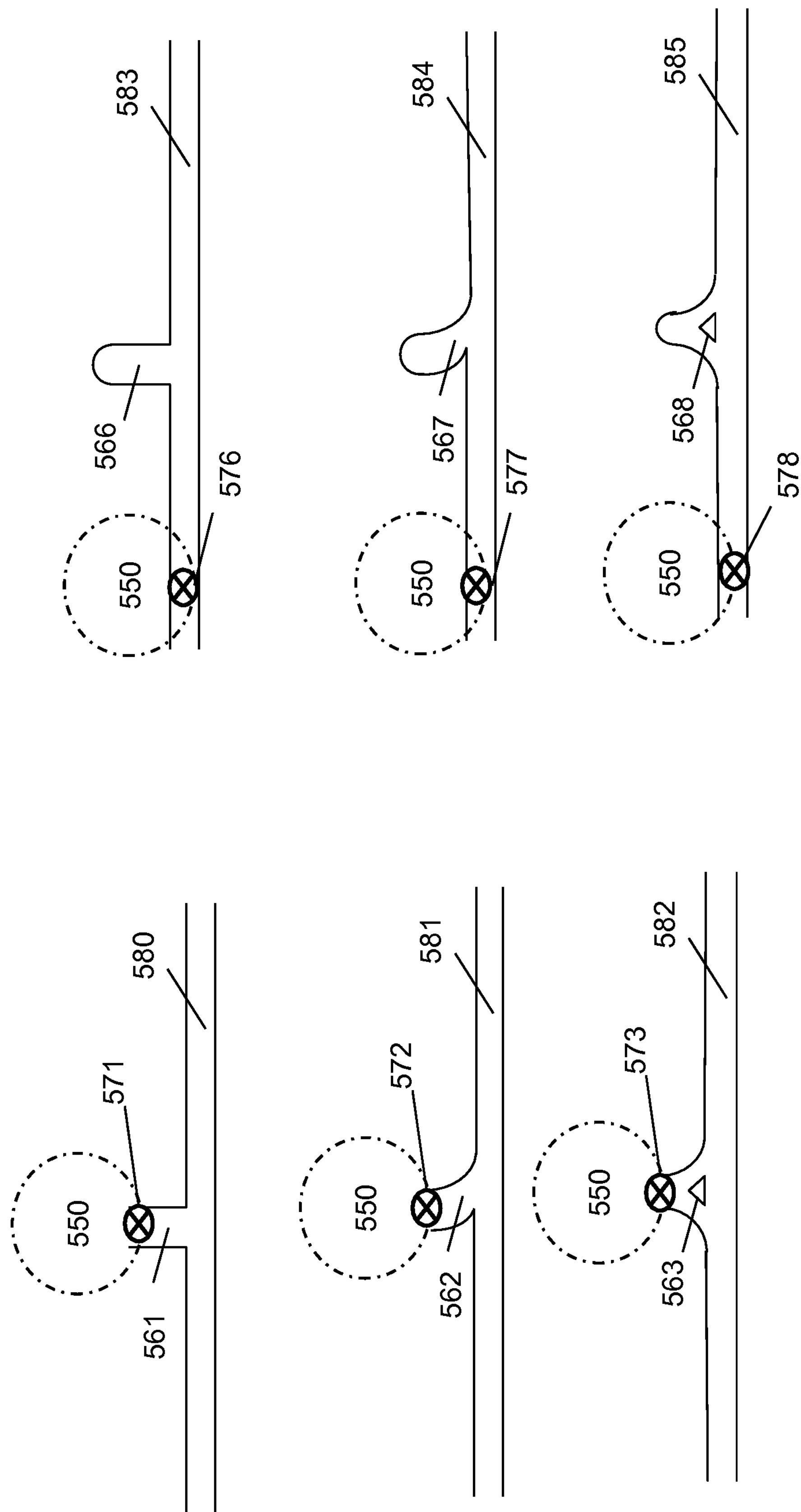
FIG. 12 illustrates diagrammatic views of linear track configurations that can be used for random access and FIFO queuing in exemplary embodiments of the present invention.

FIG. 12 shows exemplary geometries that can be used for storage locations. Track 580 has a storage location 561, placed at 90° to the main track direction. Location 571 is accessible to pipette 550. In a similar set up, track 583 has a storage location 566, accessible at a 90° angle to the main track direction. Location 576, on the main track portion of track 583, is accessible to pipette 550. Storage location 566 can be large enough to hold one or more carriers having samples. If storage location 566 is sized to allow multiple carriers to be stored, it will act as a stack where the last carrier in is the first carrier out (LIFO). A multiple storage configuration may be suitable for more complicated reordering scenarios to reduce the number of steps to reorder the queue.

Track 581 has a storage location 562, accessible via a curve. This can allow a faster exchange between the storage location and the track without requiring a sample to slow down or come to a complete stop on the main track portion before being redirected into storage location 562. Within storage location 562, location 572 is accessible to pipette 550. Similarly, track 584 has a storage position 567, accessible via a curve. Again, storage location 567 can hold one or more sample carriers. Location 577, on the main track portion, is accessible to pipette 550.

Storage location 563 is accessible to track 582 via a curved arrangement that allows a sample to enter or exit the main portion of 582 in either direction and a greater speed than might be possible with storage location 561. For example, a sample may enter storage location 563 at a brisk pace from the right and then exit storage location 563 at speed to the left. Location 573 in storage location 563 is accessible to pipette 550. Similarly, storage location 568 is accessible to track 585 via a curved arrangement that allows fast ingress or egress from either direction of the main section of track 585. Location 578 on the main track section is accessible to pipette 550.

While the examples discussed thus far have been discussed with respect to the physical location of a sample on a track section, the relationship of samples can also be understood with respect to each other. Within a queue, each sample occupies a logical position. A logical position can also be occupied by a gap in the samples. Larger gaps can also be thought of as occupying a single logical position. In this way, samples can be thought of as a linked list, having adjacent neighbors, ahead and behind one another within a track. Similarly, positions may be associated with a physical location, such as the location of a storage location. In some embodiments, multiple storage locations can be used. Physical locations can be viewed as being before, after, or between any given combination of storage locations.

FIG. 13 gives an example of states that can be considered in a queue. In each state diagram there are three rows. The top row is the identity of the storage location. The attributes that may be included in the storage location include the sample being held in the storage location, as well as the position in the queue that is currently located at the storage location.

In state 601, samples A, B, C, D, and E are on a main track in logical positions zero through 4. The storage location is aligned with logical position 2, which contains sample C. In state 602, sample C can be moved from the main queue into the storage location. This places a gap at position 2. In state 603, the queue physically moves on the track, such that samples A and B move adjacent to sample D. The queue shifts, such that the storage location aligns with logical position zero. At state 604, sample C is moved out of the storage location and into position zero. Thus, sample C has been reordered from a position between samples B and D to now be at the head of the queue. In this manner, the storage location allows random access from within the linear queue to allow samples to be handled out of the order of arrival.

FIG. 14 shows positional states that may be associated with the track handling normal priority samples and a STAT sample. In this example, the logical positions of the queue do not move with the head of the queue. Rather, the queue model associates positions with physical locations on the track. Position zero, being the head of the queue, can be associated with a pipette or probe. Position 4, being a middle position, can be associated with a storage location. By placing the storage location at the middle position of the queue, the queue can be handled in a random access fashion for up to five samples in the nine positions of the queue. Thus, where n is the number of samples in a queue, the physical track used by the queue is equal to the size of 2n−1 positions, which can be of a size suitable to contain sample carriers.

At state 611, sample A is at the head of the queue and is being aspirated via a probe/pipette. Samples B, C, and D occupy positions 1, 2, and 3. While sample A is being handled by the probe, a STAT sample arrives at position 4. In state 612, the STAT sample can be moved from position 4 to the storage location. The probe completes the aspiration of sample A. Once finished, sample A can leave the queue and move to another analyzer module within the automation system. At state 613, the remaining normal priority samples B, C, and D shift to positions 5 through 7. The STAT sample is now free to move out of the storage location into position 4, which is the logical head of the physical queue. At state 614 the queue shifts to allow the STAT sample to be handled by the probe. Samples B, C, and D once again occupy positions 1, 2, and 3. By comparing states 612 and 614, it can be seen that the storage location was used to successfully allow the STAT sample to bypass the linear queue that was present when the STAT sample arrived, without altering the physical order of the existing linear queue.

FIG. 15 shows a similar logical scenario. In contrast to FIG. 14, the scenario represented in FIG. 15 illustrates the logical flow when utilizing a storage position accessible to the track that serves both as a storage position and as an access point for a probe or pipette. In state 621, a physical queue comprising samples A, B, C, and D occupies logical positions 4, 5, 6, and 7. The storage position is associated with position 4. When a STAT sample arrives, sample A already occupies the storage location and is undergoing testing.

At state 622, sample A completes testing and is moved back to the head of the queue so that it can egress. The exit of the local track can be associated with the zeroeth logical position. Once sample A is removed from the storage location, samples B, C, and D can be shifted into positions 1, 2, and 3. This clears a path so that the STAT sample can move from position 8 to position 4 and into the storage location for immediate testing. At state 623, the STAT sample has completed testing. The remaining queue of samples B, C, and D is shifted into physical positions to the right of the storage location. This provides a clear path for the STAT sample to egress. The STAT sample is moved from the storage location and into the egress position.

Like the queue in FIG. 14, the queue in FIG. 15 allows efficient use of the local track to provide a linear queue with the random-access capabilities. Specifically, the size of the track needed to support a queue of length n is 2n−1.

FIGS. 16A and 16B illustrate an example where two storage locations can be used. Specifically, a first storage location is provided on the right-hand side at position 5. A second storage position is provided at position 2 on the left-hand side and supports access to a probe for testing a sample. In state 631, a queue of five samples occupies positions 3 through 7. In this example, a controller handling the queue determines that sample E should take priority over several samples. However, because there are not enough positions between position 0 and 2 to allow the entire linear queue to shift out of the way of sample E, the controller can reorder the queue in two steps. In state 632, the queue shifts to allow sample E to be moved into the storage location at position 5. Meanwhile, because sample E is unable to reach the probe at position 2, the controller handling the queue can make efficient use of the schedule and place sample A into the probe storage position for testing. It should be noted that in some embodiments, the shifting used to reorder the queue is faster than the time needed to test a sample. In these embodiments, the queue controller may perform multiple shifts into and out of storage locations to allow sample E to reach the head of the queue without testing other samples, such as sample A, in the interim. However, in some embodiments, testing may be relatively short compared to the amount of time required to reorder the queue. In these embodiments, intervening samples, such as sample A, can be tested while sample E is moved to the head of the queue.

At state 633, the remaining queue shifts to the right. Because the remaining queue is longer than the two positions available to the right of position 5, sample E can be moved into position 5, between samples B and C. Meanwhile, sample A can complete the testing in the probe storage location at position 2. At state 634, the linear queue shifts to the left to allow sample E to be placed at position 2 and be moved into the storage location used by the probe. Before the shift, sample A is moved out of the storage location and allowed to exit the queue to the left.

Figure 17:
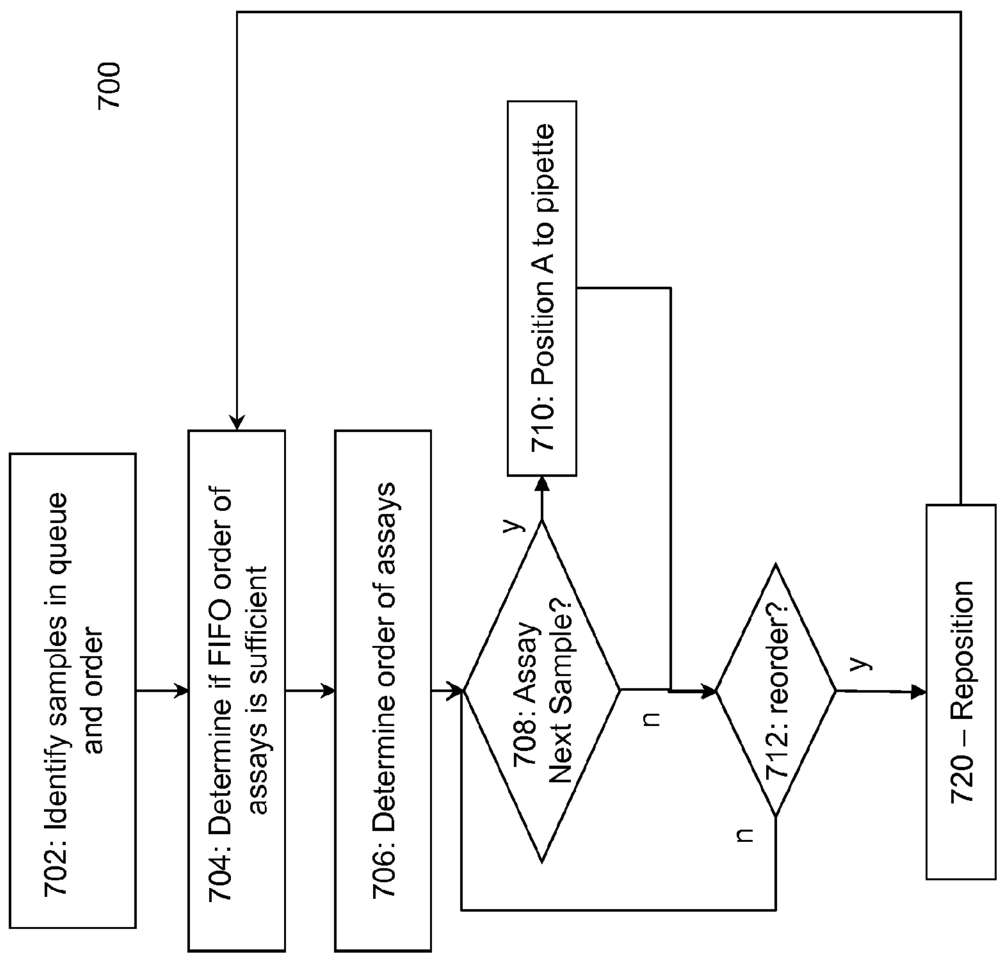
FIG. 17 is a flowchart illustrating a method for using an exemplary track for use with embodiments of the present invention.

FIG. 17 shows an exemplary method for reordering a queue. Method 700 may be performed by one or more local processors associated with an analyzer module using a linear queue. This method may also be performed by a central processor that handles multiple queues within an automation system. At step 702, the processor identifies known samples within the queue. This identification may be by any suitable means. For example, carriers may broadcast their identity via near field indication or RFID. Similarly, passive carriers can be identified by reading a barcode on the sample when the sample is moved into the local queue. Accordingly, step 702 can be performed by any suitable optical, mechanical, or electrical means available. The identification of the samples can include identifying the sample tube or the carrier that transports the sample tube. Samples and the carriers holding the samples can be considered logically interchangeable with some embodiments.

Once the samples in the queue are identified and their order has been considered, the processor can create any suitable data structures to model the queue. For example, an array, vector, linked list, database entries, etc. can be used to model the queue and/or samples. In the instance of the linked list, each sample can be an object with attributes identifying the adjacent objects to the right and the left. In a vector or array, each position of the queue can have an associated entry where the attribute in the entry is the identity of the sample.

At step 704, the processor determines whether the current order is suitable for carrying out the scheduled tests. By knowing the identity of the samples, a database can be consulted to identify the tests that are required for each sample. A scheduling processor or routine can determine one or more suitable orders of testing the samples in the queue. By determining which tests should be performed and considering the state of local resources in the analyzer, the controller can determine whether the current order makes efficient use of resources. For example, if one of the samples requires an assay that requires additional preparation of reagents, that sample may not be suitable for an early position in the queue. Similarly, the priority of the samples can be considered. If a STAT sample is identified at step 702, at step 704 it can be determined that the STAT sample needs to be at or near the head of the queue. Determining the proper order can be done in any conventional manner, using any known scheduling algorithm, including, but not limited to, those scheduling algorithms commonly used in conventional analyzers.

If the physical order of samples in the queue is sufficient, no reordering needs to take place. However, if the scheduling algorithm and comparison to the physical queue determines that samples need to be reordered, a new order can be determined at step 706. The proper order of samples at step 706 can be determined by a scheduling algorithm. In some embodiments, a scheduling algorithm determines one or more suitable candidate orders and another routine considers the resource cost necessary to create each order to select an appropriate target order. In some embodiments, the resources and time needed to create the new order can be considered as heuristic in the scheduling algorithm to select a suitable target order.

For example, as shown in FIGS. 16A-B, it may take multiple steps to reorder a single sample in the queue. If multiple samples need to be reordered, one preferred order may not be suitable when considering the time/resource constraints needed to create that order. Once a processor determines a target order, the processor can begin directing the reordering of samples. The reordering of samples can take place via a loop or other computational structure sufficient to sequentially consider the current position of sample and redirect each sample until the desired order is obtained. In some embodiments, samples can be reordered virtually in memory to verify the effectiveness of a plan to reorder samples before samples are physically reordered.

One way that the processor can determine how to properly reorder the samples is by sequentially considering each sample and determining whether or not its order is appropriate. This can be done in a virtual step before any physical changes occur. Similarly, this can also be done physically, wherein each sample is considered at the time it is simultaneously repositioned. At step 708, the first sample is considered. In this queue, the first sample is the head of the queue and may be able to freely move to a sample location for aspiration. At step 708, the processor determines if the first sample is suitable for immediate testing. If so, at step 710 a first sample (e.g., sample A) is moved into position for aspiration with a pipette. Once the sample has interacted with the pipette (or it is determined that the sample should not be moved to the pipette), at step 712, the processor considers whether that sample should be reordered. For example, a sample that requires multiple tests may remain at the head of the queue for multiple tests. However, if subsequent tests require that the sample wait for one or more testing cycles before the next test to allow the preparation of reagents, the sample at the head of the queue may need to be reordered back into the queue. Similarly, if the first sample in the queue is not suitable for the next test, it may need to be reordered. Similarly, if, after the first test, sample A should exit the queue, the necessary motion can be considered at step 712 to allow sample A to exit the queue to be released to other modules.

If no reordering is necessary, step 708 is repeated. If reordering is necessary, the queue can be reordered by repositioning the samples at step 720 using any of the reordering scenarios described herein. Once a sample is repositioned to a different location in the queue, the new order of the queue can be considered at step 704. This loop can be repeated until there are no longer any samples in the queue. Algorithm 700 can be repeated as samples arrive in the queue. During normal operation, the queue will be continuously considered and handled.

Figure 18:
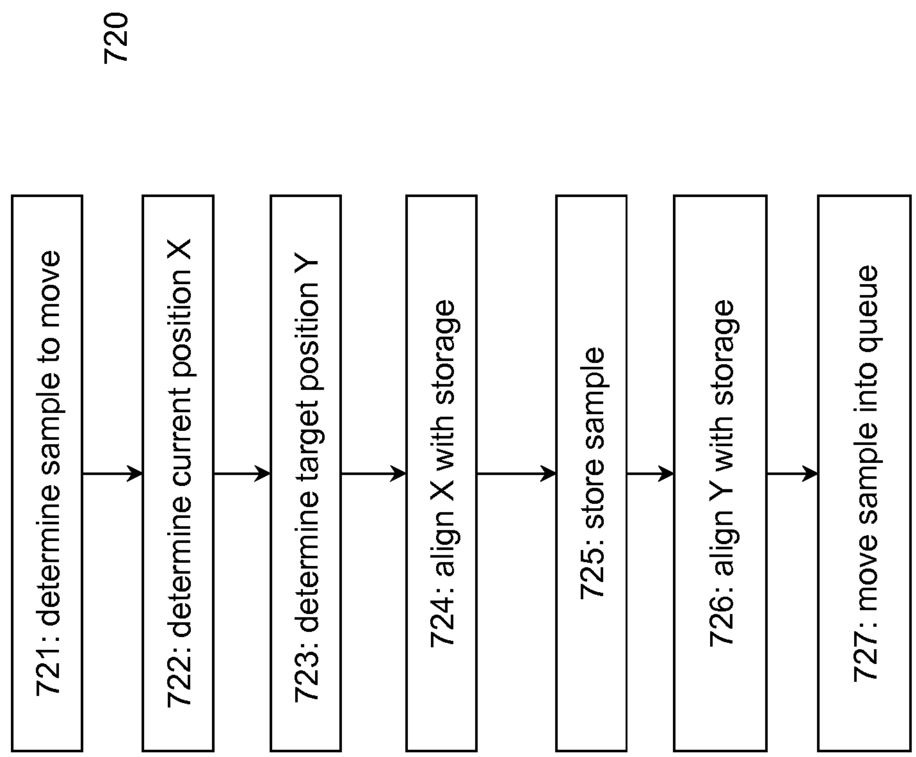
FIG. 18 is a flowchart illustrating a method for using an exemplary track for use with embodiments of the present invention.

FIG. 18 shows an exemplary embodiment of a method suitable for implementing repositioning step 720. At step 721, the processor considers which sample should be moved using a storage location. This can be determined using any known sorting algorithm that may be appropriate. Suitable sorting algorithms can include a sorting algorithm in the art that is suitable for the task. For example, some embodiments utilize a heapsort algorithm. In some embodiments, an insertion sort algorithm is used. Depending on requirements, suitable algorithms may include one or more of a bubble sort, a selection sort, an insertion sort, a shell sort, a comb sort, a merge sort, heapsort, a quicksort, a counting sort, a bucket sort, a radix sort, a distribution sort, a timsort, or any combination thereof. It will be appreciated that the use of a storage location can be adapted for use with many sorting algorithms, as it allows one or more samples to be removed and reinserted into another position in the queue.

At step 722, the current position X within the queue of a given sample is considered. At step 723, the target position Y within the queue is determined. This determination can be through any known sorting algorithm. For example, the target position Y can be the final desired position within the queue for that sample. In some instances, the target position Y can be an intermediate position (such as that shown in state 633, FIG. 16A).

At step 724, the sample and, by extension, its position within the queue, are aligned with the storage location. At step 725, the sample is moved out of its current position X and stored in storage location. At step 726, the target position Y for the sample is aligned with the storage location. At step 727, the sample is moved from the storage location into position Y in the queue. Thus, repositioning step 720 can utilize a storage position to move a given sample from a position X to a more suitable position Y to change the order of the queue. This can be repeated until any desired order is achieved.

Figure 19:
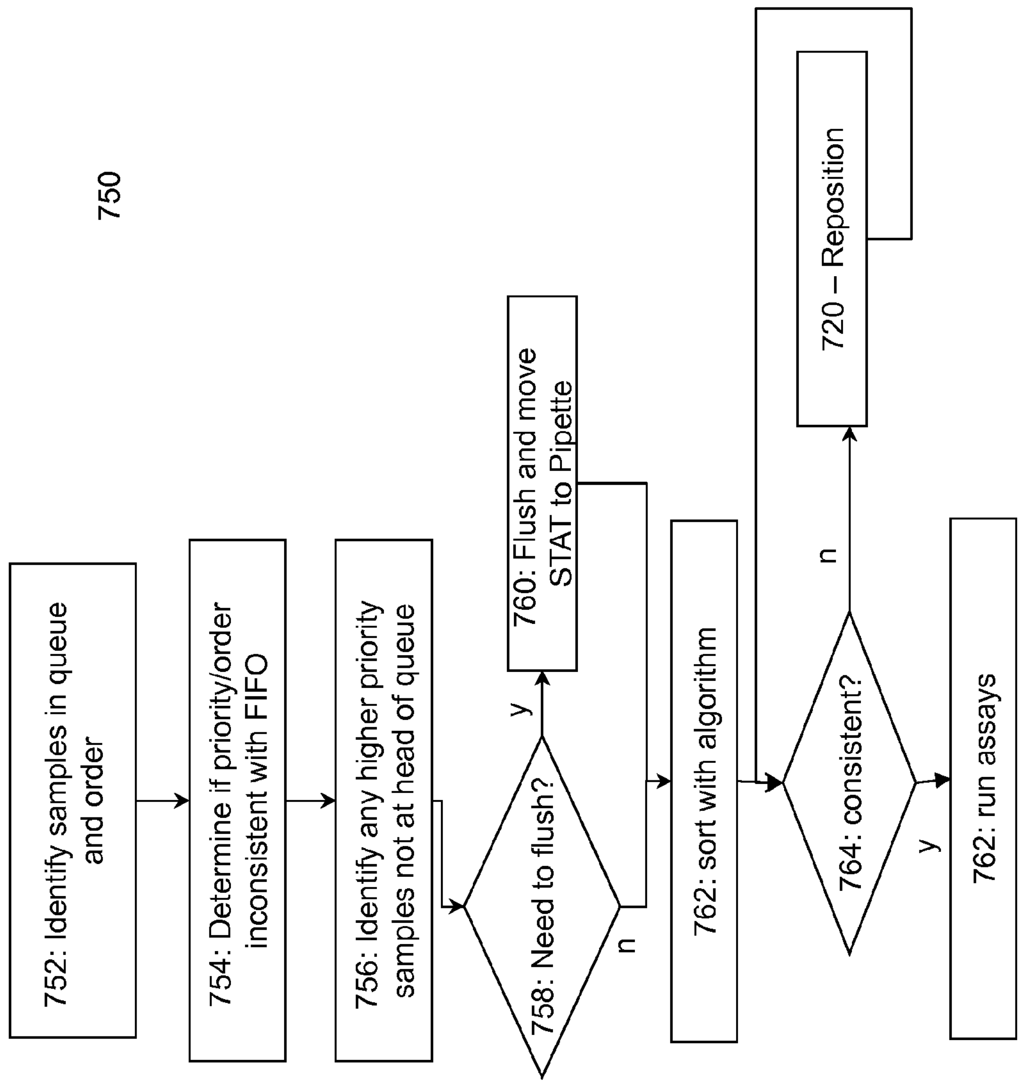
FIG. 19 is a flowchart illustrating a method for using an exemplary track for use with embodiments of the present invention.

FIG. 19 shows an exemplary method 750 for utilizing the linear random access queue approach of the present invention to handle STAT samples, as an alternative or addition to method 700 of FIG. 17. At step 752, the samples in the queue are identified and the processor handling the queue determines the current order of the samples. At step 754, the current order is considered to determine if the order is suitable for use as a FIFO queue to supply samples to a pipette/probe. If the order is not suitable, the order can be changed, as explained in method 700 in FIG. 17.

At step 756, the processor (or processors) handling the queue consider the priority of samples to assess the quality of the current order in the queue. For example, a queue can have samples of any number of priorities and the order can be adjusted to reduce the latencies of higher priority samples. In the case of STAT samples, the STAT priority can be treated as the highest priority, requiring near-immediate service of STAT samples. If a queue is in a suitable order and a STAT sample arrives, the priority can be considered at step 756. It should be noted that STAT samples already in the queue may have this priority considered at step 754 and can be considered if the order is adjusted using methods such as method 700.

After identifying any higher priority samples that are not at the head of the queue, at step 758 the processor can consider whether it is possible to reorder the queue to handle the priority samples identified. In some instances, a queue may be too long to quickly reorder the priority sample to the front within the priority rules of the system. Accordingly, in some instances in some embodiments, it may still be desirable to flush the queue rather than reorder the queue in order to meet performance requirements for handling STAT samples. If so, at step 760, the queue can be flushed to make way for the STAT sample. Flushing can be accomplished in any suitable means, including moving all samples physically through the queue without aspirating so that samples on a sidecar or pullout are pushed back out to a main track section of the automation system, where they can cycle back to the queue later. In some embodiments, flushing may include aspirating some samples in the queue if it would not add substantially to the time taken to flush the queue or if performance requirements allow sufficient time to aspirate some samples.

If no flushing is needed, at step 762 the queue can be sorted to move any higher priority samples to the head of the queue. The sorting can be accomplished by any suitable method, including those methods discussed throughout the examples herein, as well as the methods shown in FIGS. 17 and 18. At step 764, the order is considered and the processor determines if the order is consistent with priority performance requirements. If not, each sample that is not at a position consistent with priority requirements can be repositioned using the method 720. If all samples are at positions suitable for the performance requirements (e.g., STAT samples are at or near the head of the queue, while lower priority samples may be in any order if resources allow), then the processor can begin directing samples to a sample pipette to run assays.

The queues discussed herein can be managed by any suitable means, including one or more processors (e.g., a CPU, DSP, APU, GPU, single or multi-core processors, etc. along with suitable memory and hardware) that may be local and dedicated to a module, shared by modules, part of a larger central processor, or remote processors available via a network. The means could additionally, or alternatively, include dedicated circuits (e.g., ASICs, FPGAs, etc.) or other hardware suitable for creating an electrical output from sensor input. The processors or circuits can receive input about samples and/or sample carriers in the queue from memory and/or sensors to determine any status information about a queue. These processors or circuits can direct the samples and carriers holding the samples via any suitable means, including electrical/mechanical mechanisms of the automation system or local module that operates under the control or in response to the processors or circuits. In some embodiments, the electrical/mechanical mechanisms operate independently of the processors or circuits handling the queues, but the processors or circuits can send requests for motion via any suitable protocol, such as a wireless protocol, such as XBee, wired protocol, such as CAN, or other suitable means. The mechanism used to move samples and their carriers can be in any suitable form, including magnetic motion, linear motors, gears, friction surfaces, air, or pneumatic, hydraulic, or electromagnetic mechanisms. In some embodiments, the motive force is generated by the automation system, the local analyzer module, the sample carriers, or any combination thereof.

Embodiments of the present invention may be integrated with existing analyzers and automation systems. It should be appreciated that carriers may be configured in many shapes and sizes, including layouts and physical configurations suitable for use with any contemplated analyzer or instrument. For example, in some embodiments, a carrier may include multiple slots for carrying multiple samples around an automation track. One embodiment, for example, may include a physical layout of a tube-holding portion of a carrier with multiple slots in one or more transport racks. Each rack may include multiple slots (e.g., five or more slots), each slot configured to hold a tube (e.g., a sample tube).

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed:

1. An automation system for use with an automated clinical analyzer comprising:

a bidirectional track;

a plurality of sample carriers configured to move along the bidirectional track;

at least one storage location accessible to the bidirectional track; and a processor configured to sort the plurality of sample carriers by directing the carriers along the bidirectional track, and by directing at least one sample carrier into and out of the storage location to change the order of carriers with respect to the bidirectional track;

wherein the processor is configured to use an insertion sort algorithm to sort the plurality of sample carriers.

2. The automation system of claim 1, wherein at least one location of the directional track is accessible to a pipette.

3. The automation system of claim 1, wherein the storage location is configured to allow a pipette to interact with a sample carried by the at least one sample carrier.

4. The automation system of claim 1, wherein the processor is configured to use a heapsort algorithm to sort the plurality of sample carriers.

5. The automation system of claim 1, wherein the at least one storage location comprises multiple storage locations spaced apart along the bidirectional track.

6. The automation system of claim 5, wherein the processor is configured to use the multiple storage locations to sort a queue of sample carriers that is longer than the distance between two adjacent storage locations.

7. The automation system of claim 5, wherein the processor is configured to use the multiple storage locations to sort a queue of sample carriers that is longer than the distance between at least one storage location and an end of the bidirectional track.

8. The automation system of claim 1, wherein the at least one storage location is configured to store more than one of the plurality of sample carriers simultaneously.

9. The automation system of claim 1, wherein the at least one storage location comprises a track section that is perpendicular to the bidirectional track.

10. The automation system of claim 1, wherein the at least one storage location comprises a storage area that is accessible to the bidirectional track via at least one curved section of track.

11. The automation system of claim 1, wherein the bidirectional track comprises a friction track.

12. The automation system of claim 1, wherein the bidirectional track comprises a track section having electromagnetic coils to move each sample carrier.

13. The automation system of claim 1, wherein the plurality of sample carriers are configured to be independently movable.

* * * * *